US012629652B2

(12) United States Patent
Gogotsi et al.

(10) Patent No.: US 12,629,652 B2
(45) **Date of Patent: *May 19, 2026**

(54) MXene SORBENT FOR REMOVAL OF SMALL MOLECULES FROM DIALYSATE

(71) Applicants: Drexel University, Philadelphia, PA (US); University of Brighton, Brighton (GB)

(72) Inventors: Yury Gogotsi, Warminster, PA (US); Sergey Mikhalovsky, Brighton (GB); Susan R Sandeman, Brighton (GB); Babak Anasori, Fisher, IN (US); Fayan Meng, Philadelphia, PA (US)

(73) Assignees: Drexel University, Philadelphia, PA (US); University of Brighton, Brighton (GB)

( * ) Notice: Subject to any disclaimer, the term of this patent is extended or adjusted under 35 U.S.C. 154(b) by 486 days.

This patent is subject to a terminal disclaimer.

(21) Appl. No.: 18/353,257

(22) Filed: Jul. 17, 2023

(65) Prior Publication Data

US 2024/0017239 A1 Jan. 18, 2024

Related U.S. Application Data

(63) Continuation of application No. 17/670,716, filed on Feb. 14, 2022, now Pat. No. 11,772,066, which is a (Continued)

(51) Int. Cl.
*B01J 20/02* (2006.01)
*A61M 1/16* (2006.01)
(Continued)

(52) U.S. Cl.
CPC ........ *B01J 20/0211* (2013.01); *A61M 1/1656* (2013.01); *B01D 15/08* (2013.01);
(Continued)

(58) Field of Classification Search
CPC ... A61M 1/1656; A61M 1/1696; B01D 15/08; B01J 20/0211; B01J 20/0214;
(Continued)

(56) References Cited

U.S. PATENT DOCUMENTS

| | | | |
|---|---|---|---|
| 4,801,368 | A | 1/1989 | Yamashita et al. |
| 6,180,049 | B1 | 1/2001 | Jang et al. |

(Continued)

FOREIGN PATENT DOCUMENTS

| | | | |
|---|---|---|---|
| CH | 630745 | A5 | 6/1982 |
| CN | 1726608 | A | 1/2006 |

(Continued)

OTHER PUBLICATIONS

U.S. Appl. No. 17/670,716, filed Feb. 14, 2022.

(Continued)

*Primary Examiner* — Dirk R Bass
(74) *Attorney, Agent, or Firm* — BakerHostetler

(57) ABSTRACT

The present disclosure is directed to methods for scrubbing low levels of urea from aqueous solutions such as a dialysate from dialysis, and including blood and blood products, and devices capable of employing these methods.

17 Claims, 10 Drawing Sheets

Related U.S. Application Data continuation of application No. 16/633,773, filed as application No. PCT/US2018/041786 on Jul. 12, 2018, now Pat. No. 11,278,862.

(60) Provisional application No. 62/539,715, filed on Aug. 1, 2017.

(51) Int. Cl.

| | |
|---|---|
| ***B01D 15/08*** | (2006.01) |
| ***B01J 20/28*** | (2006.01) |
| ***C02F 1/28*** | (2023.01) |
| *C02F 101/38* | (2006.01) |

(52) U.S. Cl.
CPC ....... *B01J 20/0218* (2013.01); *B01J 20/0274* (2013.01); *B01J 20/28052* (2013.01); *C02F 1/281* (2013.01); *B01J 2220/42* (2013.01); *C02F 2101/38* (2013.01); *C02F 2201/006* (2013.01)

(58) Field of Classification Search
CPC ................ B01J 20/0218; B01J 20/0274; B01J 20/28052; B01J 2220/42; B01J 2220/62; C02F 1/281; C02F 2101/38; C02F 2201/006
See application file for complete search history.

(56) References Cited

U.S. PATENT DOCUMENTS

| | | | |
|---|---|---|---|
| 6,555,268 | B1 | 4/2003 | Inoue et al. |
| 6,645,612 | B2 | 11/2003 | Pujari et al. |
| 7,446,190 | B2 | 11/2008 | Sadelain et al. |
| 7,527,859 | B2 | 5/2009 | Zhong et al. |
| 7,964,938 | B2 | 6/2011 | Yoon et al. |
| 7,976,941 | B2 | 7/2011 | Lodyga et al. |
| 8,226,801 | B2 | 7/2012 | Zhamu et al. |
| 9,193,595 | B2 | 11/2015 | Barsoum et al. |
| 10,720,644 | B2 | 7/2020 | Barsoum et al. |
| 11,411,218 | B2 | 8/2022 | Barsoum et al. |
| 2002/0068488 | A1 | 6/2002 | Tuller et al. |
| 2003/0073769 | A1 | 4/2003 | Pujari et al. |
| 2003/0148184 | A1 | 8/2003 | Omaru et al. |
| 2003/0224168 | A1 | 12/2003 | Mack et al. |
| 2004/0048157 | A1 | 3/2004 | Neudecker et al. |
| 2004/0076856 | A1 | 4/2004 | Hugosson |
| 2004/0229028 | A1 | 11/2004 | Sasaki et al. |
| 2006/0140839 | A1 | 6/2006 | Maniccia et al. |
| 2007/0065725 | A1 | 3/2007 | Inoue et al. |
| 2007/0066503 | A1 | 3/2007 | Basaly |
| 2009/0017332 | A1 | 1/2009 | Kisi et al. |
| 2010/0236937 | A1 | 9/2010 | Rosvall et al. |
| 2010/0322909 | A1 | 12/2010 | Okada et al. |
| 2011/0017585 | A1 | 1/2011 | Zhamu et al. |
| 2011/0045223 | A1 | 2/2011 | Lin et al. |
| 2011/0104464 | A1 | 5/2011 | Pyzik et al. |
| 2012/0021224 | A1 | 1/2012 | Everett et al. |
| 2012/0247800 | A1 | 10/2012 | Shah et al. |
| 2013/0048339 | A1 | 2/2013 | Tour et al. |
| 2013/0092428 | A1 | 4/2013 | Kawaguchi et al. |
| 2013/0210218 | A1 | 8/2013 | Accardi et al. |
| 2014/0162130 | A1 | 6/2014 | Barsoum et al. |
| 2015/0210044 | A1 | 7/2015 | Barsoum et al. |
| 2015/0305212 | A1 | 10/2015 | Sarto et al. |
| 2015/0306570 | A1 | 10/2015 | Mayes et al. |
| 2015/0321147 | A1 | 11/2015 | Fleming et al. |
| 2016/0336088 | A1 | 11/2016 | Barsoum et al. |
| 2017/0190925 | A1 | 7/2017 | Wu et al. |
| 2018/0021499 | A1 * | 1/2018 | Natan .................. C07C 275/02 604/29 |
| 2022/0085224 | A1 | 3/2022 | Nabet et al. |
| 2022/0363916 | A1 | 11/2022 | Gogotsi et al. |
| 2024/0365522 | A1 | 10/2024 | Gogotsi et al. |
| 2024/0402389 | A1 | 12/2024 | Gogotsi et al. |
| 2024/0417581 | A1 | 12/2024 | Kim et al. |
| 2025/0004341 | A1 | 1/2025 | Gogotsi et al. |
| 2025/0011244 | A1 | 1/2025 | Gogotsi et al. |
| 2025/0015209 | A1 | 1/2025 | Ghidiu et al. |

FOREIGN PATENT DOCUMENTS

| | | | |
|---|---|---|---|
| CN | 101891141 | A | 11/2010 |
| CN | 101916859 | A | 12/2010 |
| CN | 104733712 | A | 6/2015 |
| CN | 106024416 | A | 10/2016 |
| CN | 106986316 | A | 7/2017 |
| EP | 0948067 | A1 | 10/1999 |
| EP | 1381099 | A1 | 1/2004 |
| JP | 08-078018 | A | 3/1996 |
| JP | 10-112316 | A | 4/1998 |
| JP | 2005-158725 | A | 6/2005 |
| JP | 2007-214137 | A | 8/2007 |
| JP | 2008-078115 | A | 4/2008 |
| JP | 2013-142109 | A | 7/2013 |
| WO | 02/39468 | A2 | 5/2002 |
| WO | 02/81372 | A2 | 10/2002 |
| WO | 02/96799 | A2 | 12/2002 |
| WO | 2005/007566 | A2 | 1/2005 |
| WO | 2006/112869 | A2 | 10/2006 |
| WO | 2007/093011 | A1 | 8/2007 |
| WO | 2007/121931 | A2 | 11/2007 |
| WO | 2008/073529 | A2 | 6/2008 |
| WO | 2009/063031 | A2 | 5/2009 |
| WO | 2009/091826 | A2 | 7/2009 |
| WO | 2010/093598 | A2 | 8/2010 |
| WO | 2010/128492 | A1 | 11/2010 |
| WO | 2011/086391 | A1 | 7/2011 |
| WO | 2012/120264 | A1 | 9/2012 |
| WO | 2012/177712 | A1 | 12/2012 |
| WO | 2014/088995 | A1 | 6/2014 |
| WO | 2015/132764 | A1 | 9/2015 |
| WO | 2016/049109 | A2 | 3/2016 |
| WO | 2016/126596 | A2 | 8/2016 |
| WO | 2017/011044 | A2 | 1/2017 |

OTHER PUBLICATIONS

U.S. Appl. No. 16/633,773, filed Jan. 24, 2020.

Abbasi et al., "Preparation of Silver Nanowires and Their Application in Conducting Polymer Nanocomposites", Materials Chemistry and Physics, 2015, 166, 1-15.

Agulhon et al., Structural Regime Identification in lonotropic Alginate Gels: Influence of the Cation Nature and Alginate Structure, Biomacromolecules 2012, 13, 215-220.

Agulhon et al., Structure of Alginate Gels: Interaction of Diuronate Units with Divalent Cations from Density Functional Calculations, Biomacromolecules 2012, 13, 1899-1907.

Al-Ghamdi et al., "New Electromagnetic Wave Shielding Effectiveness at Microwave Frequency of Polyvinyl Chloride Reinforced Graphite/Copper Nanoparticles", Composites Part A: Applied Science and Manufacturing, 2010, 41, 1693-1701.

Al-Saleh et al., "Copper Nanowire/Polystyrene Nanocomposites: Lower Percolation Threshold and Higher EMI Shielding", Composites Part A: Applied Science and Manufacturing, 2011, 42, 92-97.

Alhabeb et al., MXene films and composites for EMI shielding, stealth planes/boats, metamaterials, invisibility cloaks and other related applications, A.J. Drexel Nanomaterials Institute and Department of Materials Science & Engineering, Drexel University, Philadelphia, PA 19104, USA, 2011, pp. 1-10.

Ameli et al., "Electrical Properties and Electromagnetic Interference Shielding Effectiveness of Polypropylene/Carbon Fiber Composite Foams", Carbon, 2013, 60, 379-391.

Ameli et al., "Lightweight Polypropylene/Stainless-Steel Fiber Composite Foams with Low Percolation for Efficient Electromagnetic Interference Shielding", ACS Applied Materials & Interfaces, 2014, 6, 11091-11100.

(56) References Cited

OTHER PUBLICATIONS

Arjmand et al., "Outstanding Electromagnetic Interference Shielding of Silver Nanowires: Comparison with Carbon Nanotubes", RSC Advances, 2015, 5, 56590-56598.
Augustyn, V., et al., "High-rate electrochemical energy storage through Li+ intercalation pseudocapacitance," Nature Materials, vol. 12, No. 6, Apr. 14, 2013, pp. 518-522.
B.-W. Li, Y. Shen, Z .- X. Yue and C.-W. Nan, Applied Physics Letters, 2006, 89, 132504.
Barsoum et al., "Room-Temperature Deintercalation and Self-Extrusion of Ga from Cr2GaN", Science, May 7, 1999, 284(5416), 937-939.
Barsoum et al., "The Topotactic Transformation of Ti3SiC2 into a Partially Ordered Cubic Ti(C0.67Si0.06) Phase by the Diffusion of Si into Molten Cryolite", Journal of the Electrochemical Society, 1999, 146(10), 3919-3923.
Barsoum, "Physical Properties of the MAX phases", Encyclopedia of Materials: Science and Technology, 2006, 11 pages.
Barsoum, et al., "Synthesis and Characterization of a Remarkable Ceramic: Ti3SiC2," J Amer. Chem. Soc., 1996 79(7), 1953-1956.
Barsoum, M. and El-Raghy, T., "The MAX Phases: Unique New Carbide and Nitride Materials", American Scientist, Jul.-Aug. 2001, 89:334-343.
Barsoum, M. W., "MAX phases: Properties of machinable ternary carbides and nitrides," Properties of Materials, John Wiley & Sons, Sep. 2013, pp. 1-436.
Barsoum, M., "The MN+1AXN phases: New Class Of Solids", Progress In Solid State Chemistry, Jan. 1, 2000, 28(1-4), 201-281.
Bayat et al., "Electromagnetic Interference Shielding Effectiveness of Hybrid Multifunctional Fe3O4/carbon Nanofiber Composite", Polymer, 2014, 55, 936-943.
Chang, F., et al., "Synthesis of a new graphene-like transition metal carbide by de-intercalating Ti3AlC2," Materials Letters, vol. 109, Oct. 15, 2013, pp. 295-298.
Chaudhary et al., "Lightweight and Easily Foldable MCMB-MWCNTs Composite Paper With Exceptional Electromagnetic Interference Shielding", ACS Applied Materials & Interfaces, 2016, 8, 16, 10600-10608.
Chen et al., "Microstructure and Phase Transformation of Ti 3 AC 2 (A= Al, Si) In Hydrofluoric Acid Solution", Crystal Research and Technology, Oct. 27, 2014, 49(10), 813-819.
Chen et al., "In-situ synthesis of Ti3AlC2/TiC—Al2003 composite from TiO2—Al—C system", Journal of Materials Science & Technology, 2006, 22, 455-458.
Chen et al., "High-Performance Epoxy Nanocomposites Reinforced with Three-Dimensional Carbon Nanotube Sponge for Electromagnetic Interference Shielding", Advanced Functional Materials, 2016, 26, 447-455.
Chen et al., "Lightweight and Flexible Graphene Foam Composites for High-Performance Electromagnetic Interference Shielding", Advanced Materials, 2013, 25, 1296-1300.
Coleman et al., "Two-Dimensional Nanosheets Produced by Liquid Exfoliation of Layered Materials", Science, Feb. 4, 2011, 331, 568-571.
Conway, B. E., "Electrochemical supercapacitors: Scientific fundamentals and technological applications," Kluwer Academic/plenum Publishers, 1999, pp. 1-698.
Cover et al., "A comprehensive survey of M2AX phase elastic properties", Journal of Physics: Condensed MatterInstitute of physics publishing, bristol, GB, vol. 21, No. 30, Jul. 29, 2009, p. 305403.
Crespo et al., "Synergistic Effect of Magnetite Nanoparticles and Carbon Nanofibers in Electromagnetic Absorbing Composites", Carbon, 2014, 74, 63-72.
Dall'agnese et al. High capacitance of surface-modified 2D titanium carbide in acidic electrolyte. Electrochemistry Communications vol. 48, pp. 118-122. Available Online Sep. 16, 2014 [retrieved on Nov. 9, 2015]. Retrived from internet: <URL: http://nano.materials.drexel.edu/wp-content/uploads/2013/02/1-s2.0-S1388248114002896-main. pdf>.
De Bellis et al., "Electromagnetic Properties of Composites Containing Graphite Nanoplatelets at Radio Frequency", Carbon, 2011, 49, 4291-4300.
Eis, PS et al., Accumulation of miR-155 and BIC RNA in Human B Cell Lymphomas. Proceedings of the National Academy of Sciences of the United States of America, Mar. 8, 2005, 102(10), 3627-3632, Abstract.
Eklund et al., "The Mn+1AXn Phases: Materials Science and Thin-Film Processing", Thin Solid Films, 2010, 518, 1851-1878.
El-Tantawy et al., "New Functional Conductive Polymer Composities Containing Nickel Coated Carbon Black Reinforced Phenolic Resin", Macromolecular Research, 2005, 13, 194-205.
Enyashin, A. N., et al., "Two-dimensional titanium carbonitrides and their hydroxylated derivatives: Structural, electronic properties and stability of MXenes Ti3C2-xNx(OH)2 from DFTB calculations," Journal of Solid State Chemistry, vol. 207, Nov. 2013, pp. 42-48.
Ettmayer et al., "Crystal structure of Cr3(C,N)2 and CrVC2", Monatshefle fur Chemie und Verwandte Teile Anderer Wissenschaflen, Jul. 1966, vol. 97, Issue 4, 1258-1262.
European Patent Application No. 12803351.1: Supplementary European Search Report dated Jan. 30, 2015, 14 pages.
Fang et al., "Layer-Structured Silver Nanowire/Polyaniline Composite Film as a High Performance X-band EMI Shielding Material", Journal of Materials Chemistry C, 2016, 4, 4193-4203.
Finkel et al., "Magnetotransport properties of the ternary carbide Ti3SlC2: Hall effect, magnetoresistance, and magnetic susceptibility", Physical Review B, Jan. 15, 2002, vol. 65, Issue 3, 4 pages.
Fugetsu et al., "Electrical conductivity and electromagnetic interference shielding efficiency of carbon nanotube/cellulose composite paper", Carbon 46, 2008, 1253-1269.
Gargama et al., "Polyvinylidene Fluoride/Nickel Composite Materials for Change Storing, Electromagnetic Interference Absorption, and Shielding Applications", Journal of Applied Physics, 2015, 117, 224903.
Ghaffari, M., et al. High-volumetric performance aligned nanoporous microwave exfoliated graphite oxide-based electrochemical capacitors, Adv. Mater, vol. 25, Issue 35, Sep. 20, 2013, pp. 4879-4885.
Ghidiu et al., "Conductive two-dimensional titanium carbide 'clay' with high volumetric capacitance", Nature, Dec. 2014, 516, 78-81.
Gogotsi, Y., et al., "True performance metrics in electrochemical energy storage," Science, vol. 334, Issue 6058, Nov. 18, 2011, pp. 917-918.
H. S. S. Ramakrishna Matte et al: "MoS2 and WS2 Analogues of Graphene", Angewandte Chemie International Edition, vol. 49, No. 24, Apr. 28, 2010 pp. 4059-4062.
Halim et al., "Transparent Conductive Two-Dimensional Titanium Carbide Epitaxial Thin Films", Chem. Mater., 2014, vol. 26, No. 7, 2374-2381, Abstract; p. 2376, Scheme 1, p. 2379, col. 1, para. 2; p. 2379, col. 2, para. 2.
Hendaoui, et al., Ti—Al—C Max Phases by Aluminothermic Reduction Process, International Journal of Self-Propagating High-Temperature Synthesis, 17 (2008) 125-128.
Hensen, E. J. et al., "Why clays swell?," J. Phys. Chem. B, vol. 106, Issue 49, Nov. 14, 2002, pp. 12664-12667.
Hsiao et L., "Lightweight and flexible reduced graphene oxide/water-borne polyurethane composites with high electrical conductivity and excellent electromagnetic interference shielding performance", ACS Applied Materials & Interfaces, 2014, 6, 13, 10667-10678.
Hu et al. "Two-dimensional Sc2C: A reversible and high-capacity hydrogen storage material predicted by first principles calculations", International Journal of Hydrogen Energy, Jul. 2014, 39,20, 10606-10612.
Novel Electronic and Magnetic Properties of Two-Dimensional Transition Metal Carbides and Nitrides, Khazaei et al., Adv. Funct. Mater. 2013, 23, 2185-2192.
Wenderoth et al., "Synergism on Electromagnetic Inductance (EMI)-shielding in metal-and-ferroelectric-particle filled polymers", Polymer Composites, 1989, 10, 52-56.
X. Huang, B. Dai, Y. Ren, J. Xu and P. Zhu, J. Nanomaterials, 2015, 2015, 2-2.

(56) References Cited

OTHER PUBLICATIONS

Xiao, Han et al., "Studies on the Synthesis and Microwave Absorption Properties of Fe3 O4/polyaniline FGM", Physica Scripta, 2007, 2007, 335.
Xie, X,. et al., "Surface Al leached Ti3AlC2 substituting carbon for catalyst support served in a harsh corrosive electrochemical system," Nanoscale, vol. 6, No. 19, Oct. 7, 2014, pp. 11035-11040.
Xu et al., "Synthesis of Electromagnetic Functionalized Barium Ferrite Nanoparticles Embedded in Polypyrrole", The Journal of Physical Chemistry B, 2008, 112, 2775-2781.
Yan et al., "Efficient Electromagnetic Interference Shielding of Lightweight Graphene/Polystyrene Composite", Journal of Materials Chemistry, 2012, 22, 18772-18774.
Yan et al., "Structured Reduced Graphene Oxide/Polymer Composites for Ultra-Efficient Electromagnetic Interference Shielding", Advanced Functional Materials, 2015, 25, 559-566.
Yang et al., "Conductive Carbon Nanofiber-Polymer Foam Structures", Advanced Materials, 2005, 17, 1999-2003.
Yang et al., "Novel Carbon Nanotube-Polystyrene Foam Composites for Electromagnetic Interference Shielding" Nano Letters, 2005, 5, 2131-2134.
Yang, X., et al., "Liquid-mediated dense integration of graphene materials for compact capacitive energy storage," Science, vol. 341, Issue 6145, Aug. 2, 2013, pp. 534-537.
Yao et al., "Flammability Properties and Electromagnetic Interference Shielding of PVC/graphene Composites Containing Fe3O4 Nanoparticles", RSC Advances, 2015, 5, 31910-31919.
Yuan et al., "Design of Artificial Nacre-Like Hybrid Films as Shielding to Mitigate Electromagnetic Pollution", Carbon, 2014, 75, 178-189.
Yuchang et al., "Graphene Nanosheets/BaTiO 3 ceramics as highly efficient electromagnetic interference shielding materials in the X-band", Journal of Materials Chemistry C, 2016, 4, 371-375.
Zeng et al., "Lightweight and Anisotropic Porous MWCNT/WPU composites for ultrahigh performance electromagnetic interference shielding", Advanced Functional Materials, 2016, 26, 303-310.
Zeng et al., "Thin and Flexible multi-walled carbon nanotube/waterborne polyurethane composites with high-performance electromagnetic interference shielding", Carbon, 2016, 96, 768-777.
Zhang et al., "Recent Research and Applications of (Ti12xAlx)N Thin Hard Coating", Journal of Synthetic Crystals, Jun. 2007, p. 700.
Zhang et al., "Nitrogen-doped Graphdiyne Applied for Lithum-ion Storage", ACS applied materials & interfaces, 2016, 8, 13, 8467-8473.
Zhang et al., "Preparation and Characterization of Graphene Paper for Electromagnetic Interference Shielding", Carbon, 2015, 82, 353-359.
Zheng, J. P., et al., "Hydrous ruthenium oxide as an electrode material for electrochemical capacitors," J. Electrochemical Society, vol. 142, No. 8, Aug. 1995, pp. 2699-2703.
Hu et al., "Mo 2 Ga 2 C: a new ternary nanolaminated carbide", Chemical Communications, vol. 51, No. 30, Mar. 4, 2015, pp. 6560-6563.
Hu et al., "MXene: A New Family of Promising Hydrogen Storage Medium", J. Phys. Chem A,2013, 117, 14523-14260.
Hu et al., "Supplementary Information for Mo2Ga2C: a new ternary nanolaminated carbide", Chemical Communications, Mar. 4, 2015, pp. 1-5.
Hu, C., "Low Temperature Thermal Expansion, High Temperature Electrical Conductivity, and Mechanical Properties of Nb4AlC3 Ceramic Synthesized by Spark Plasma Sintering", Journal of Alloys and Compounds, Nov. 13, 2009, 487(1-2), 675-681.
Huang et al., "The Influence of Single-Walled Carbon Nanotube Structure on the Electromagnetic Interference Shielding Efficiency of its Epoxy Composites", Carbon, 2007, 45, 1614-1621.
International Patent Application No. PCT/US13/072733: The International Search Report and The Written Opinion dated Mar. 28, 2014, pp. 1-12.
International Patent Application No. PCT/US13/64503: The International Search Report and The Written Opinion dated Jan. 24, 2014, pp. 1-13.
J et al: "A Non-Aqueous Asymmetric Cell with a Ti 2 C-Based Two-Dimensional Negative Electrode", A1368 Journal of The Electrochemical Society, Jan. 1, 2012, pp. 1368-1373.
Jiang et al., "Facile, Green and Affordable Strategy for Structuring Natural Graphite/Polymer Composite with Efficient Electromagnetic Interference Shielding", RSC Advances, 2015, 5, 22587-22592.
Jin et al., "Synthesis of VC—Cr3C2 Nanocomposite Powders by Carbothermal Reduction", Nanoscience and Nanotechnology Letters, Oct. 2012, vol. 4, No. 10, 1028-1030, Abstract, 1 page.
Jiwu Shang et al: "Fabrication and dielectric properties of oriented polyvinylidene fluoride nanosheets", Materials Chemistry and Physics, Elsevier SA, Switerland, Taiwan, Republic of China, vol. 134, No. 2, Mar. 23, 2012 pp. 867-874.
Jung, I., et al., "Tunable electrical conductivity of individual graphene oxide sheets reduced at "low" temperatures," Nano Lett, vol. 8, issue 12, Nov. 1, 2008, pp. 4283-4287.
Korzhavyi et al., "Ab Initio Study of Phase Equilibria in TiC.sub.x", Physical Review Letters, Dec. 18, 2001, 88(1), 1-4.
Krueger et al., "Synergistic Effects of Carbon Fillers on Shielding Effectiveness in Conductive Nylon 6, 6-and Polycarbonate-Based Resins", Advances in polymer Technology, 2003, 22, 96-111.
Kuester et al., "Processing and Characterization of Conductive Composites Based on poly(styrene-b-ethylene-ran-butylene-b-styrene) (SEBS) and Carbon additives: A Comparative study on expanded graphite and carbon Black", Composites Part B: Engineering, 2016, 84, 236-247.
Kulkarni et al., Thermal Expansion and Stability of Ti2SC in Air and Inert Atmospheres, Journal of Alloys and Compounds, 2009, 469, 395-400.
Kumar et al., "Large-Area Reduced Graphene Oxide thin film with excellent thermal conductivity and Electromagnetic Interference Shielding Effectiveness", Carbon, 2015, 94, 494-500.
Levi, M. D., et al., "Solving the capacitive paradox of 2D MXene by electrochemical quartz-crystal admittance and in situ electronic conductance measurements," Advance Energy Materials, vol. 5, Issue 1, Aug. 8, 2014, pp. 11.
Li et al., "Synthesis and thermal stability of two-dimensional carbide MXene Ti3C2", Materials Science and Engineering, vol. 191, 2015, pp. 33-40.
Li et al., "Electrical and Mechanical Properties of Electronically Conductive Polyethersulfone Composites", Composites, 1994, 25, 215-224.
Li et al., "Facile Synthesis and properties of ZnFe2O4 and ZnFe2O4/polypyrrole core-shell nanoparticles", Solid State Sciences, 2009, 11, 1319-1324.
Li et al., "Lightweight and highly conductive aerogel-like carbon from sugarcane with superior mechanical and EMI shielding Properties", ACS Sustainable Chemistry & Engineering, 2015, 3, 1419-1427.
Li et al., "Making polymeric membranes antifouling via "grafting from", polymerization of zwitterions", Journal of Applied Polymer Science, 2015, 132, 41781.
Li et al., "Ultrathin carbon foams for effective electromagnetic interference shielding", Carbon, 2016, 100, 375-385.
Liang et al., "Electromagnetic interference shielding of graphene/epoxy composites", Carbon, 2009, 47, 922-925.
Ling et al., "Flexible and conductive MXene films and nanocomposites with high capacitance", PNAS, Nov. 25, 2014, vol. 111, No. 47, 16676-16681, Supporting Information.
Ling et al., "Facile Preparation of Lightweight Microcellular Polyetherimide/graphene composite foams for electromagnetic interference shielding", ACS Applied Materials & Interfaces, 2013, 5, 2677-2684.
Lis, D., et al., "Liquid flow along a solid surface reversibly alters interfacial chemistry," Science, vol. 344, Issue 6188, Jun. 6, 2014, pp. 1138-1142.
Lukatskaya et al., "Cation Intercalation and High Volumetric Capacitance of Two- Dimensional Titanium Carbide", Science, vol. 341, No. 6153, Sep. 27, 2013, pp. 1502-1505, & "Supplementary Mate-

(56) References Cited

OTHER PUBLICATIONS rials - Cation Intercalation and High Volumetric Capacitance of Two-Dimensional Titanium Carbide", Science, vol. 341, No. 6153, Sep. 26, 2013, pp. 1-15.
Machine translation of JP2013142109, Pub. Date 2013.
Madsen, F. T., et al., "The swelling behaviour of clays," Applied, Clay Science, vol. 4, Issue 2, Jun. 1989, pp. 143-156.
Makino et al., "Characterization of Zr—Al—N films synthesized by a magnetron sputtering method", Surface & Coatings Technology, 193 (2005) 219-222.
Mashtalir, O., et al., "Intercalation and delamination of layered carbides and carbonitrides," Nature Communications, vol. 4, Issue 1, Apr. 16, 2013, pp. 24.
Mashtalir, O., et al., "Kinetics of aluminum extraction from Ti3AlC2 in hydrofluoric acid," Materials Chemistry and Physics, vol. 139, Issue 1, Apr. 15, 2013, pp. 147-152.
Miller, J., et al., "Electrochemical capacitors for energy management," Materials Science, vol. 321, No. 5889, Sep. 2008, pp. 651-652.
Mishra et al., "Conducting Ferrofluid: a high-performance microwave shielding material", Journal of Materials Chemistry A, 2014, 2, 13159-13168.
Mogilevsky et al., "The Structure of Multilayered Titania Nanotubes Based on Delaminated Anatase", Chemical Physics Letters, 2008, 460, 517-520.
Moglie "Electromagnetic Shielding Performance of Carbon Foams", et al., Carbon, 2012, 50, 1972-1980.
Murali, S., et al., "Volumetric capacitance of compressed activated microwave-expanded graphite oxide (a-MEGO) electrodes," Nano Energy, vol. 2, Feb. 7, 2013, pp. 764-768.
Myhra, et al., "Crystal-Chemistry of the TbAlC2 and Tl4AlN Layered Carbide/Nitride Phases-Characterization by XPS", Journal of Physics and Chemistry of Solids, Apr. 2001, vol. 62(4), 811-817.
Nadeau, "Clay Particle Engineering: a Potential New Technology with Diverse Applications", Applied Clay Science, Mar. 1987, 2, 83-93.
Naguib et al., "Mxene: A Promising Transition Metal Carbide Anode for Lithium-ion Batteries", Electrochemistry Communications, Mar. 2012, 16, 61-64.
Naguib et al., "New Two-dimensional Niobium and Vanadium Carbides as Promising Materials for Li-Ion Batteries", American Chemical Society, Oct. 2013, 135(43), 15966-15969.
Naguib et al., Synthesis of a New Nanocrystalline Titanium Aluminum Fluoride Phase By Reaction of Ti2aic With Hydrofluoric Acid, RSC Adv.1: 1493-1499, 2011. [retrieved on Mar. 7, 2014]. Retrieved from the internet: <URL:http://pubs.rsc.org.ezproxy.neu.ed u/en/Content/Articlelanding/2011/RA/c1ra00390a#/div, Abstract.
Naguib et al., "Two-Dimensional Nanocrystals Produced by Exfoliation of Ti.sub.3AlC.sub.2", Advanced Materials, 2011, 23, 4248-4253.
Naguib et al., "Two-Dimensional Transition Metal Carbides", American Chemical Society, Feb. 2012, 6(2), 1322-1331.
Naguib et al., "Mxenes: A new family of two-dimensional materials", Advanced Materials, 2014, 26, 992-1005.
Naguib, M., et al., "Two-dimensional nanocrystals produced by exfoliation of Ti3AlC2," Advanced Materials, vol. 23, Issue 37, Oct. 4, 2011, pp. 4248-4253.
Nan et al., "Percolation phenomena in niobium-doped TiC1-x", Materials Science and Engineering B-Solid State Materials for Advanced Technology, Feb. 1991, vol. 7, Issue 4, 283-286.
Nicolosi, V., et al., "Liquid exfoliation of layered materials," Science, vol. 340, Issue 6139, 2013, pp. 19.
Ning et al., "Two-dimensional nanosheets of MoS2: A promising material with high dielectric properties and microwave absorption performances", Nanoscale, 2015, 7, 15734-15740.
Ohlan et al., "Microwave Absorption behavior of core-shell structured poly (3, 4-ethylenedioxy thiophene)—Barium Ferrite Nanocomposites", ACS Applied Materials & Interfaces, 2010, 2, 927-933.
Panwar et al., "Analysis of electrical, dielectric, and electromagnetic interference shielding behavior of graphite filled high density polyethylene composites", Polymer Engineering & Science, 2008, 48, 2178-2187.
Peng et al., "Unique lead adsorption behavior of activated hydroxyl group in two-dimensional titanium carbide", Journal of The American Chemical Society, 2014, 136, 4113-4116.
Rao et al., "A Study of The Synthetic Methods and Properties of Graphenes", Science and Technology of Advanced Materials, 11, Oct. 27, 2010, 1-15.
Rao et al., "Single-Layer Graphene-Assembled 3D Porous Carbon Composites with PVA and Fe 3 O 4 nano-fillers: an interface-mediated superior dielectric and EMI shielding", Physical Chemistry Chemical Physics, 2015, 17, 18353-18363.
Rudy, "Crystal structure of Ta2VC2", Journal of the Less-Common Motale, Jan. 1970, vol. 20, Issue 1, 49-55.
S. H. Hosseini and A. Asadnia, J. Nanomaterials, 2012, 2012, 3-3.
Sachdev et al., "Electromagnetic Interference Shielding of Graphite/Acrylonitrile Butadiene Styrene Composites", Journal of Applied Polymer Science, 2011, 120, 1100-1105.
Savoskin et al., "Carbon Nanoscrolls Produced From Acceptor-Type Graphite Intercalation Compounds", 2007, Carbon, 45, 2797-2800.
Schmidt, et al., "XPS Studies of Amino Acids Absorbed on Titanium Dioxide Surfaces", Fresenius Journal of Analytical Chemistry, May 1991, 341, 412-415.
Shahzad et al., "Biomass-Derived Thermally Annealed Interconnected Sulfur-Doped Graphene as a Shield Against Electromagnetic Interference", ACS Applied Materials & Interfaces, 2016, 8, 9361-9369.
Shahzad et al., "Sulfur doped graphene/polystyrene nanocomposites for electromagnetic interference shielding", Composite Structures, 2015, 133, 1267-1275.
Shen et al., "Compressible Graphene-Coated Polymer Foams with Ultralow Density for Adjustable Electromagnetic Interference (EMI) Shielding," ACS Appl. Mater. Interfaces, vol. 8, 2016, pp. 8050-8057.
Shen et al., "Lightweight, Multifunctional Polyetherimide/Graphene@Fe3O4 Composite Foams for Shielding of Electromagnetic Pollution", ACS Applied Materials & Interfaces, 2013, 5, 11383-11391.
Shen et al., "Microcellular graphene foam for improved broadband electromagnetic interference shielding", Carbon, 2016, 102, 154-160.
Shen et al., "Ultrathin flexible graphene film: An Excellent thermal conducting material with efficient EMS shielding", Advanced Functional Materials, 2014, 24, 4542-4548.
Shui et al., "Nickel filament polymer-matrix composites with low surface impedance and high electromagnetic interference shielding effectiveness", Journal of Electronic Materials, 26, 928-934.
Simon, P., et al., "Materials for electrochemical capacitors," Nature Materials, vol. 7, Dec. 2008, pp. 845-854.
Simon, P., et al., "Where do batteries end and supercapacitors begin?," Science, vol. 343, Mar. 14, 2014, pp. 1210-1211.
Singh et al., "Encapsulation of y-Fe 2 O 3 decorated reduced graphene oxide in polyaniline core-shell tubes as an exceptional tracker for electromagnetic environmental pollution", Journal of Materials Chemistry A, 2014, 2, 3581-3593.
Singh et al., "Nanostructured graphene/Fe 3 O 4 incorporated polyaniline as a high performance shield against electromagnetic pollution", Nanoscale, 2013, 5, 2411-2420.
Singh et al., "Phenolic resin-based composite sheets filled with mixtures of reduced graphene oxide, y-Fe2O3 and carbon fibers for excellent electromagnetic interference shielding in the X-band", Carbon, 2012, 50, 3868-3875.
Singh et al., "Poly (3,4-ethylenedioxythiophene) y-Fe2O3 polymer composite-super paramagnetic behavior and variable range hopping 1D conduction mechanism-synthesis and Characterization", Polymers for Advanced Technologies, 2008, 19, 229-236.
Singh et al., "Probing the engineered sandwich network of vertically aligned carbon nanotube-reduced graphene oxide composites for high performance electromagnetic interference shielding applications", Carbon, 2015, 85, 79-88.

(56) References Cited

OTHER PUBLICATIONS

Song et al., "Flexible graphene/polymer composite films in sandwich structures for effective electromagnetic interference shielding", Carbon, 2014, 66, 67-76.
Song et al., "Interfacial engineering of carbon nanofiber-graphene-carbon nanofiber heterojunctions in flexible lightweight electromagnetic shielding networks", ACS Applied Materials & Interfaces, 2014, 6, 10516-10523.
Song et al., "Magnetic and conductive graphene papers toward thin layers of effective electromagnetic shielding", Journal of Materials Chemistry A, 2015, 3, 2097-2107.
Spanier et al., "Vibrational Behavior of the Mn+1AXn phases from First-Order Raman Scattering „M=Ti , V,Cr, A=Si, X=C,N)", Physical Review B, Jan. 2005, 71, 1-4.
Srinivasan, "Batteries for Advanced Transportation Technologies (BATT) Program. The fourth quarter 2014 FY report", Berkeley National Laboratory Document, Nov. 19, 2014, http://bmr.lbl.gov/wp-content/uploads/sites/3battfiles/reports/BATT_2014_-4th_Quarterly_Report.pdf, 74 pages.
Stankovich et al., "Graphene-based Composite Materials", Nature, Jul. 2006, 442, 282-286.
Su et al., "High-Cuality Thin Graphene Films from Fast Electrochemical Exfoliation", ACS Nano, 2011,5(3), 2332-2339.
Sui et al., "The Synthesis of three-dimensional (3D) Polydopamine-functioned carbonyl ion powder@polypryrrole (CIP@PPy) Aerogel Composites for Excellent Microwave Absorption", Synthetic Metals, Dec. 2015, vol. 210, Part B, pp. 156-164.
Tang et al., "Are MXenes Promising Anode Materials for Li Ion Batteries? Computational Studies on Electronic Properties and Li Storage Capability of Ti.sub.3C.sub.2 and Ti.sub.3C.sub.2X.sub.2 (X=F, OH) Monolayer", Journal of the American Chemical Society, 2012, 134, 16909-16916.
Tao, Y., et al., "Towards ultrahigh volumetric capacitance: graphene derived highly dense but porous carbons for supercapacitors," Scientific Report, vol. 3, Issue 1, Oct. 17, 2013, pp. 8.
Thore, Phase stability and physical properties of nanolaminated materials from first principles, Link ping Studies in Science and Technology Dissertation No. 1742, 2016.
Tran et al., "Lithium Intercalation in Porous Carbon Electrodes", Material Research Society 1995 Spring Meeting, San Francisco, CA, Apr. 17-21, 1995, 12 Pages.
Travaglini et al., "The Corrosion Behavior of Ti3SiC2 in Common Acids and Dilute NaOH", Corrosion Science, Jun. 1, 2003, 45(6), 1313-1327.
Tripathi et al., "High yield Synthesis of Electrolyte heating assisted electrochemically exfoliated graphene for electromagnetic interference shielding applications", RSC Advances, 2015, 5, 19074-19081.
Tzenov et al., "Synthesis and Characterization of Ti3AlC2", Journal of the American Ceramic Society, Jan. 1, 2000, 83(4), 825-832.
Umrao et al., "Microwave-Assisted Synthesis of Boron and Nitrogen co-doped Reduced Graphene Oxide for the Protection of Electromagnetic Radiation in Ku-Band", ACS Applied Materials & Interfaces, 2015, 7, 19831-19842.
Varshney et al., "In Situ Synthesis of Polypyrrole-y-Fe2O3-Fly Ash Nanocomposites for Protection against EMI Pollution", Industrial & Engineering Chemistry Research, 2014, 53, 14282-14290.
Verma et al., "Barium Ferrite Decorated Reduced Graphene Oxide Nanocomposite for Effective Electromagnetic Interference Shielding", Physical Chemistry Chemical Physics, 2015, 17, 1610-1618.
Viculis et al., "A Chemical Route to Carbon Nanoscrolls", Science, Feb. 28, 2003, 299, p. 1361.
Viculis, et al., "Intercalation and Exfoliation Routes to Graphite Nanoplatelets", Journal of Materials Chemistry, 2005, vol. 15, 974-978.
Wang, J., et al., "Pseudocapacitive contributions to electrochemical energy storage in TiO2 (anatase) nanoparticles," J. Phys. Chem. C, vol. 111, Issue 40, Sep. 18, 2007, pp. 14925-14931.
Wen et al., "High Performance electromagnetic Interference Shielding of Lamellar MoSi2/glass composite coatings by plasma spraying", Journal of Alloys and Compounds, 2016, 666, 359-365.
Wen et al., "Reduced Graphene Oxides: Light-Weight and High-Efficiency Electromagnetic Interference Shielding at Elevated Temperatures", Advanced Materials, 2014, 26, 3484-3489.
Wen et al., "Reduced Graphene Oxides: The Thinnest and Most Lightweight Materials with Highly Efficient Microware Attenuation Performances of the Carbon World", Nanoscale, 2014, 6, 5754-5761.

* cited by examiner

MXene SORBENT FOR REMOVAL OF SMALL MOLECULES FROM DIALYSATE

CROSS REFERENCE TO RELATED APPLICATIONS

This application is a Continuation of U.S. patent application Ser. No. 17/670,716, filed Feb. 22, 2022 (now allowed), which is a Continuation of U.S. patent application Ser. No. 16/633,773, filed Jan. 24, 2020 (now U.S. Pat. No. 11,278,862, issued Mar. 22, 2022), which is the National Stage Application of International Patent Application No. PCT/US2018/041786, filed Jul. 12, 2018, which claims priority to U.S. Provisional Application No. 62/539,715, filed Aug. 1, 2017, the contents of which applications are incorporated by reference herein in their entireties for any and all purposes.

TECHNICAL FIELD

The present disclosure is directed to the purification of blood and blood products, for example for the treatment of renal failure or chronic kidney failure.

BACKGROUND

Chronic renal failure or chronic kidney failure is a condition when a large number of compounds that are normally excreted by the kidneys remain in the body. Urea is one of the crucial nitrogen-containing metabolites in biological system. However, when the kidneys fail, it remains in the body. Increased blood urea nitrogen (BUN) is associated with kidney disease or failure. Once kidney function drops to life threatening levels, hemodialysis is used as a proven, safe procedure to remove excess fluid, electrolytes and the majority of small, water soluble molecules including urea by diffusion through a semipermeable porous membrane into the dialysate fluid. However, hemodialysis is by no means optimized. It is time-consuming, cumbersome and mobility-restricting. Miniaturization of the presently employed hemodialysis systems into high effective, portable and low-cost devices (i.e., a Wearable Artificial Kidney "WAK") has been under development for some time in order to provide flexibility for dialysis patients. One of the most challenging aspects in the development of a portable dialysis device is in the efficient removal of urea, whose removal rate can be used to assess the efficiency of dialysis treatment. Urea removal can also reflect efficient removal of small ionic species such potassium as well.

In chronic kidney disease ("CKD") patients, pre-dialysis serum urea levels are significantly higher than the normal range rising to between 20 and 40 mg/dL, while the urea concentration in dialysate is around 30 mg/dL. Miniaturization of the presently employed hemodialysis systems into highly effective, portable and low-cost devices (i.e., a Wearable Artificial Kidney "WAK") has been under development for some time based on peritoneal dialysis (PD), hemofiltration (HF) and hemodialysis (HD). Again, one of the most challenging aspects in the development of a WAK is in the efficient removal of urea.

However, in WAK based on PD, urea is cleansed enzymatically using the enzyme urease, which finally converts urea into toxic ammonia and carbon dioxide. Thus, the sorbent system for PD must contain zirconium phosphate to remove ammonia, but zirconium phosphate also adsorbs potassium, calcium, magnesium and other cations and metals, and in doing so removes some necessary electrolytes also releasing undesirable hydrogen ions for which then another sorbent is needed. Zirconium carbonate is a kind of adsorbent which can adsorb hydrogen ions, but the adsorption is by ion exchange, so it releases bicarbonate, acetate, and to a lesser extent sodium; for HF to provide effective clearance, large ultrafiltration volumes with the corresponding return of large volumes of a replacement fluid are required. For a WAK based on HD to provide effective clearance, the sorbents used are in effect ion exchangers, that release bicarbonate and sodium. Moreover, the main disadvantage of a wearable HD device is that there is a risk of clotting in the extracorporeal circuit. These concerns about the disadvantages of recently-developed WAK systems, make the discovery of an adsorbent that adsorbs urea without causing other side effects desirable.

Additionally, a variety of medical condition treatments, including liver diseases, renal disease, hereditary urea cycle abnormalities, heart failure and dietary problems, require selective adsorption of small molecules, such as urea, from blood or blood plasma.

Carbon sorbents that are conventionally used for detoxification, cannot efficiently adsorb urea. Currently no materials capable of effectively adsorbing urea are available.

The present invention is directed to addressing at least some of these deficiencies.

SUMMARY

MX-enes are a new class of two-dimensional (2D) transition metal carbides and nitrides that were discovered at Drexel University in 2011. Over the past few years, the range of materials contained within this family has expanded to include more than about 20 different MXenes. To date, most of the applications of MXenes focus on energy storage systems and their catalytic properties due because of their rich surface chemistries and high electronic conductivities. However, MXenes offer a large surface area and superior adsorptive potential for heavy metal ions and other materials.

Embodiments of the present invention(s) include methods of removing urea from solutions, each method comprising removing urea from an initial aqueous solution of urea, the method comprising subjecting the aqueous solution of urea to a MXene composition, at ambient or near ambient temperatures and conditions, so that urea is reduced from an initial concentration in the initial solution to a final concentration in a final solution. In some embodiments, the initial concentration of urea in the initial aqueous solution is in a range of from 10 mmol/L to 1000 mmol/L, or is initially in a concentration range from 10 mg/dL to 100 mg/dL, or around 30 mg/dL, and the final concentration is at least 10% less than the initial concentration.

In certain of further embodiments, the MXene composition is described as a composition comprising at least one layer having first and second surfaces, each layer described by a formula $M_{n+1}X_n T_x$ and comprising:

- a substantially two-dimensional array of crystal cells,
- each crystal cell having an empirical formula of $M_{n+1}X_n$, such that each X is positioned within an octahedral array of M,
- wherein M is at least one Group IIIB, IVB, VB, or VIB metal,
- wherein each X is C, N, or a combination thereof;
- n=1, 2, or 3; and wherein
- $T_x$ represents surface termination groups.

In other of these embodiments, the MXene composition is described as a composition comprising at least one layer having first and second surfaces, each layer comprising:

a substantially two-dimensional array of crystal cells, each crystal cell having an empirical formula of $M'_2M''_nX_{n+1}$, such that each X is positioned within an octahedral array of M' and M'', and where $M''_n$ are present as individual two-dimensional array of atoms intercalated (sandwiched) between a pair of two-dimensional arrays of M' atoms, wherein M' and M'' are different Group IIIB, IVB, VB, or VIB metals (especially where M' and M'' are Ti, V, Nb, Ta, Cr, Mo, or a combination thereof), wherein each X is C, N, or a combination thereof; and n=1 or 2.

Variations of these MXene compositions and structures are provided herein.

The methods described herein are selective for adsorbing urea, and other defined small molecules and ions, and in various aspects, the aqueous solution further comprises amino acids, polypeptides, or blood plasma proteins, or one or more types of blood cells such as erythrocytes (red blood cells, RBCs), leukocytes (white blood cells), or thrombocytes (platelets), or one or more of such substances as glucose, fatty acids, and lactic acid. The aqueous solution may consist of or comprise blood or a blood product (e.g., blood serum, dialysate), and the ambient or near ambient temperatures and conditions used do not compromise the utility of the blood or blood product for later use by a human patient.

The methods are suitable for use in dialyses equipment, including portable dialysis equipment, both in through-pass and recycle modes.

Additional embodiments include those devices useful for operating the inventive methods, including those devices for removing urea from an aqueous solution of urea, the device comprising an exchangeable cartridge of MX-ene composition through which the solution is directed to pass, the passage adapted to allow the urea solution to contact the MX-ene composition contained in the cartridge.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings:

FIG. 1A shows a comparison to control of the changes in the urea weight upon adsorption using two-dimensional (2D) titanium carbide MXene ($Ti_3C_2T_x$) as adsorbent with different mass-loadings (5.000, 2.500, 1.250, 0.625, 0.312 and 0.155 g—adsorbent dosage). FIG. 1B shows the removal efficiency in % using $Ti_3C_2T_x$ as adsorbent with different mass-loadings (5.000, 2.500, 1.250, 0.625, 0.312 and 0.155 g—adsorbent dosage). FIG. 1C shows the amount of urea adsorbed during the adsorption time using 2D titanium carbide ($Ti_3C_2T_x$ circles and $Ti_2CT_x$, triangles) and molybdenum titanium carbide ($Mo_2TiC_2T_x$, squares) MXene (mass-loading was 0.155 g). FIG. 1D shows a comparison to control of the changes in the urea weight upon adsorption using 2D titanium carbide ($Ti_3C_2T_x$ and $Ti_2CT_x$) and molybdenum titanium carbide ($Mo_2TiC_2T_x$) (mass-loading was 0.155 g and adsorption time was 4 minutes). The volume of liquid phase containing urea for the adsorption was 6 mL with the initial concentration ~30 mg/dL.

FIG. 2A shows changes in the urea concentration upon adsorption using two-dimensional (2D) titanium carbide MXene ($Ti_3C_2T_x$) as adsorbent with different mass-loadings (5.000, 2.500, 1.250, 0.625, 0.312 and 0.155 g—adsorbent dosage). FIG. 2B shows removal efficiency in % using $Ti_3C_2T_x$ as adsorbent with different mass-loadings (5.000, 2.500, 1.250, 0.625, 0.312 and 0.155 g—adsorbent dosage). FIG. 2C shows the amount of urea adsorbed during the adsorption time using 2D titanium carbide ($Ti_3C_2T_x$, squares and $Ti_2CT_x$, circles) and molybdenum titanium carbide ($Mo_2TiC_2T_x$, triangles) MXene (mass-loading was 0.155 g). FIG. 2D shows a comparison of the changes in the urea concentration upon adsorption using 2D titanium carbide ($Ti_3C_2T_x$ and $Ti_2CT_x$) and molybdenum titanium carbide ($Mo_2TiC_2T_x$) (mass-loading was 0.625 g and adsorption time was 4 minutes). The volume of dialysate for the adsorption was 6 mL with the initial concentration ~30 mg/dL.

FIG. 3A shows the most stable adsorption configurations and binding energies for each orientation of urea on the surfaces of MXenes. FIG. 3B shows the difference of charge density for parallel urea on the surfaces of MXenes; The turquoise and yellow regions indicate depletion and accumulation of electrons, respectively.

FIG. 4A shows configurations and distances between two layers of MXenes before and after intercalation of urea. FIG. 4B shows interactions between MXene surface and protonated urea FIGS. 5A-D $^1H$ NMR spectra.

DETAILED DESCRIPTION OF ILLUSTRATIVE EMBODIMENTS

Figure 1A:
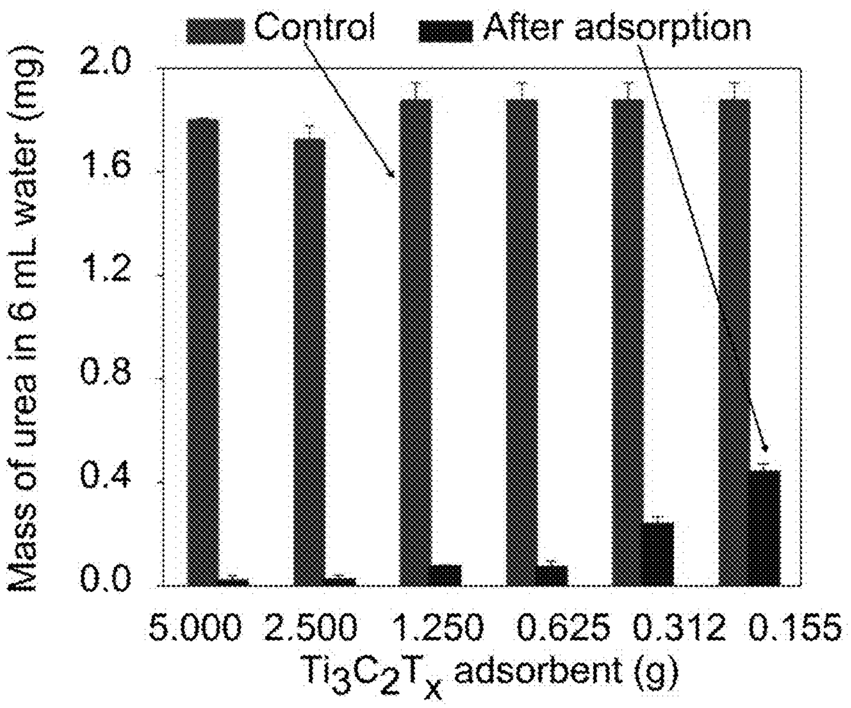
FIGS. 1A-D show a comparison of urea uptake capacities from aqueous solution.

The present invention is directed to methods for polishing low levels of urea from aqueous solutions, including blood and blood products, dialysate from dialysis devices, and devices which may be used to employ these methods. Some of these embodiments are described in the appended claims. Contacting aqueous solutions of urea with MX-ene materials has been disclosed in one or more U.S. and international patent applications, for example, U.S. patent application Ser. No. 14/094,966 ("the '966 application," filed Dec. 13, 2013), now U.S. Pat. No. 9,193,585. In contrast with the present disclosure, the aim in these previous disclosures was to prepare the resulting intercalated product in which the urea intercalated into the MX-ene composition, and the conditions were considerably more forcing than described herein. For example, in the '966 application, the conditions used to prepare the urea-intercalated MX-ene were described as contacting 5 mL of 50 wt. % aqueous solution of urea with 0.3 g of $Ti_3C_2T_x$ and stirred for 24 h at 60° C. In the instant disclosure, the removal of the urea from the aqueous solutions is better characterized as a polishing step, to remove low levels of urea from aqueous solutions (including blood and blood products) at ambient or near ambient temperatures (e.g., at or about 25° C.) over the course of minutes (e.g., in some cases, less than 5 minutes). At the levels described herein, urea is initially present at concentrations less than 1 mol/L. At these levels (1 mol/L of urea in water is equivalent to 60 g urea/L solution or about 6 wt %) the urea is present initially at levels which are more than an order of magnitude lower than the forcing conditions previously described. In other embodiments disclosed herein, urea can be removed from both aqueous urea solutions and dialysate directly from the uremic patients, wherein the initial urea concentration is about 30 mg/dL or 0.3 g urea/L solution, or more than 3 orders of magnitude lower than the forcing conditions described above. The results indicated that the adsorption can reach the equilibrium in less than 5 minutes. Nothing in the previous disclosures even suggests that MX-enes would be able to remove urea from solution with the surprising efficiency of kinetics and equilibrium constants necessary to affect the removals described herein. In particular, the contrast of the conditions previously used for urea with those used to intercalate other materials compounds further suggests that MXenes would require extremely forcing conditions to adsorb urea. Further, nothing in the previous references suggests any benefit of reacting MX-ene with urea solutions of such low concentrations or mild conditions. The methods described in this present disclosure are both remarkable and surprising in the face of the previous disclosures.

Embodiments of the present invention(s) include methods of removing urea from solutions, each method comprising subjecting the aqueous solution of urea to a MXene composition, at ambient or near ambient temperatures, so as to remove urea even from low level urea solutions, in effect "polishing" these aqueous solutions so as to reduce the concentration even further. In some embodiments, the urea is reduced from an initial concentration in the initial solution to a final concentration in a final solution, wherein the initial concentration of urea in the initial aqueous solution is in a range of from 10 to 20 mmol/L, from 20 to 40 mmol/L, from 40 to 80 mmol/L, from 80 to 160 mmol/L, from 160 to 200 mmol/L, from 200 to 400 mmol/L, from 400 to 600 mmol/L, from 600 to 800 mmol/L, from 800 to 1000 mmol/L, or in a range that is defined by two or more of these ranges, or is initially in a concentration range from 5 to 10 mg/dL, from 10 to 15 mg/dL, from 15 to 20 mg/dL, from 20 to 25 mg/dL, from 25 to 30 mg/dL, from 30 to 35 mg/dL, from 35 to 40 mg/dL, from 40 to 45 mg/dL, from 45 to 50 mg/dL, from 50 to 55 mg/dL, from 55 to 60 mg/dL, from 60 to 70 mg/dL, from 70 to 80 mg/dL, from 80 to 90 mg/dL, from 90 to 100 mg/dL, or in a range that is defined by two or more of these ranges, and the final concentration is at least 10%, 20%, 30%, 40%, 50%, 60%, 70%, 80%, or 90% less than the initial concentration. In independent embodiments, the final concentration of the urea in the final solution is less than 100 mmol/L, less than 80 mmol/L, less than 60 mmol/L, less than 40 mmol/L, less than 20 mmol/L, less than 10 mmol/L, less than 5 mmol/L, or less than 1 mmol/L, or any combination of two or more of these ranges. In some cases, the levels of urea may even be undetectable by standard analytical methods. Specific exemplary ranges and levels, both initial and final, are described in the Examples.

It is convenient to measure these levels by any number of quantitative or semi-quantitative analytical methods, though $^1$H-NMR and liquid chromatography, including high performance liquid chromatography (HPLC) and other chemical reaction coupled colorimetric and fluorometric methods, have been shown to be especially useful in this regard. Commercial Urea Assay Kits may also be used to measure the concentrations of urea.

These MXene compositions described herein are also sometimes described in terms of the phrase "MX-enes" or "MX-ene compositions." MXenes may be described as two-dimensional transition metal carbides, nitrides, or carbonitrides comprising at least one layer having first and second surfaces, each layer described by a formula $M_{n+1}X_n T_x$ and comprising:

a substantially two-dimensional array of crystal cells, each crystal cell having an empirical formula of $M_{n+1}X_n$, such that each X is positioned within an octahedral array of M, wherein M is at least one Group IIIB, IVB, VB, or VIB metal, wherein each X is C, N, or a combination thereof;

n=1, 2, or 3; and wherein $T_x$ represents surface termination groups.

These so-called MXene compositions have been described in U.S. Pat. No. 9,193,595 and Application PCT/US2015/051588, filed Sep. 23, 2015, each of which is incorporated by reference herein in its entirety at least for its teaching of these compositions, their (electrical) properties, and their methods of making. That is, any such composition described in this application is considered as applicable for use in the present methods and within the scope of the present invention. For the sake of completeness, M can be at least one of Sc, Y, Lu, Ti, Zr, Hf, V, Nb, Ta, Cr, Mo, or W. In certain embodiments in this class, M is at least one Group IVB, Group VB, or Group VIB metal, preferably Ti, Mo, Nb, V, or Ta. Certain of these compositions include those having one or more empirical formula wherein $M_{n+1}X_n$ comprises $Sc_2C$, $Ti_2C$, $V_2C$, $Cr_2C$, $Cr_2N$, $Zr_2C$, $Nb_2C$, $Hf_2C$, $Ti_3C_2$, $V_3C_2$, $Ta_3C_2$, $Ti_4C_3$, $V_4C_3$, $Ta_4C_3$, $Sc_2N$, $Ti_2N$, $V_2N$, $Cr_2N$, $Cr_2N$, $Zr_2N$, $Nb_2N$, $Hf_2C$, $Ti_3N_2$, $V_3C_2$, $Ta_3C_2$, $Ti_4N_3$, $V_4C_3$, $Ta_4N_3$ or a combination or mixture thereof. In particular embodiments, the $M_{n+1}X_n$ structure comprises $Ti_3C_2$, $Ti_2C$, $Ta_4C_3$ or $(V_{1/2}Cr_{1/2})_3C_3$. In some embodiments, M is Ti or Ta, and n is 1, 2, or 3, for example having an empirical formula $Ti_3C_2$ or $Ti_2C$. In some of these embodiments, at least one of said surfaces of each layer has surface terminations comprising hydroxide, oxide, sub-oxide, or a combination thereof. In certain preferred embodiments, the MXene composition is described by a formula $M_{n+1}X_n T_x$, where $M_{n+1}X_n$ are $Ti_2CT_x$, $Mo_2TiC_2T_x$, $Ti_3C_2T_x$, or a combination thereof, and $T_x$ is as described herein. Those embodiments wherein M is Ti, and n is 1 or 2, preferably 2, are especially preferred.

In other embodiments, the methods use compositions, wherein the two-dimensional transition metal carbide, nitrides, or carbonytride comprises a composition having at least one layer having first and second surfaces, each layer comprising:

a substantially two-dimensional array of crystal cells, each crystal cell having an empirical formula of $M'_2M''_nX_{n+1}$, such that each X is positioned within an octahedral array of M' and M", and where $M''_n$ are present as individual two-dimensional array of atoms intercalated (sandwiched) between a pair of two-dimensional arrays of M' atoms, wherein M' and M" are different Group IIIB, IVB, VB, or VIB metals (especially where M' and M" are Ti, V, Nb, Ta, Cr, Mo, or a combination thereof), wherein each X is C, N, or a combination thereof, preferably C; and n=1 or 2.

These compositions are described in greater detail in Application PCT/US2016/028354, filed Apr. 20, 2016, which is incorporated by reference herein in its entirety at least for its teaching of these compositions and their methods of making. For the sake of completeness, in some embodiments, M' is Mo, and M" is Nb, Ta, Ti, or V, or a combination thereof. In other embodiments, n is 2, M' is Mo, Ti, V, or a combination thereof, and M" is Cr, Nb, Ta, Ti, or V, or a combination thereof. In still further embodiments, the empirical formula $M'_2M''_nX_{n+1}$ comprises $Mo_2TiC_2$, $Mo_2VC_2$, $Mo_2TaC_2$, $Mo_2NbC_2$, $Mo_2Ti_2C_3$, $Cr_2TiC_2$, $Cr_2VC_2$, $Cr_2TaC_2$, $Cr_2NbC_2$, $Ti_2NbC_2$, $Ti_2TaC_2$, $V_2TaC_2$, or $V_2TiC_2$, preferably $Mo_2TiC_2$, $Mo_2VC_2$, $Mo_2TaC_2$, or $Mo_2NbC_2$, or their nitride or carbonitride analogs. In still other embodiments, $M'_2M''_nX_{n+1}$ comprises $Mo_2Ti_2C_3$, $Mo_2V_2C_3$, $Mo_2Nb_2C_3$, $Mo_2Ta_2C_3$, $Cr_2Ti_2C_3$, $Cr_2V_2C_3$, $Cr_2Nb_2C_3$, $Cr_2Ta_2C_3$, $Nb_2Ta_2C_3$, $Ti_2Nb_2C_3$, $Ti_2Ta_2C_3$, $V_2Ta_2C_3$, $V_2Nb_2C_3$, or $V_2Ti_2C_3$, preferably $Mo_2Ti_2C_3$, $Mo_2V_2C_3$, $Mo_2Nb_2C_3$, $Mo_2Ta_2C_3$, $Ti_2Nb_2C_3$, $Ti_2Ta_2C_3$, or $V_2Ta_2C_3$, or their nitride or carbonitride analogs.

Each of these compositions having empirical crystalline formulae $M_{n+1}X_n$ or $M'_2M''_nX_{n+1}$ are described in terms of comprising at least one layer having first and second surfaces, each layer comprising a substantially two-dimensional array of crystal cells. In some embodiments, these compositions comprise layers of individual two-dimensional cells. In other embodiments, the compositions comprise a plurality of stacked layers. Additionally, in some embodiments, at least one of said surfaces of each layer has surface terminations (optionally designated "$T_s$" or "$T_x$") comprising alkoxide, carboxylate, halide, hydroxide, hydride, oxide, sub-oxide, nitride, sub-nitride, sulfide, thiol, or a combination thereof. In some embodiments, at least one of said surfaces of each layer has surface terminations comprising alkoxide, fluoride, hydroxide, oxide, sub-oxide, or a combination thereof. In still other embodiments, both surfaces of each layer have said surface terminations comprising alkoxide, fluoride, hydroxide, oxide, sub-oxide, or a combination thereof. As used herein the terms "sub-oxide," "sub-nitride," or "sub-sulfide" is intended to connote a composition containing an amount reflecting a sub-stoichiometric or a mixed oxidation state of the M metal at the surface of oxide, nitride, or sulfide, respectively. For example, various forms of titania are known to exist as $TiO_x$, where x can be less than 2. Accordingly, the surfaces of the present invention may also contain oxides, nitrides, or sulfides in similar sub-stoichiometric or mixed oxidation state amounts.

In the methods, these MXenes may comprise simple individual layers, a plurality of stacked layers, or a combination thereof. Each layer may independently comprise surfaces functionalized by any of the surface coating features described herein (e.g., as in alkoxide, carboxylate, halide, hydroxide, hydride, oxide, sub-oxide, nitride, sub-nitride, sulfide, thiol, or a combination thereof) or may be also partially or completely functionalized by polymers, either on the surface of individual layers, for example, where the two-dimensional compositions are embedded within a polymer matrix, or the polymers may be intercalated between layers to form structural composites, or both.

The methods may be applied to aqueous solutions, including physiologically important aqueous fluids, with or without the need to remove extraneous (e.g., non-urea) materials. In certain embodiments, in addition to the urea, the aqueous solution further comprises amino acids, polypeptides, or blood plasma proteins. Further, the aqueous solution may further comprise one or more of types of blood cells such as erythrocytes (red blood cells, RBCs), leukocytes (white blood cells), or thrombocytes (platelets). Still further, the aqueous solution may also comprise one or more of substances such as glucose, fatty acids, and lactic acid.

The methods are useful in a dialysis context—i.e., where the aqueous solution is or comprises blood or a blood product (e.g., blood serum, dialysate). That is, the methods are operable at ambient or near ambient temperatures and under conditions suitable so as not to compromise the utility of the blood or blood product for later use by a human patient. In these aspects, the initial urea concentrations are physiologically relevant to a human patient.

In some aspects of the present invention(s), the methods comprise contacting the aqueous urea solutions with fresh or previously used MXene compositions. Likewise, the aqueous solutions may be contacted with one or more fresh batches of MXene materials, for example, where the final aqueous solution of urea of a first pass cleaning is contacted with previously unexposed (i.e., fresh) MXene compositions.

"Contacting" may comprise adding MXene compositions into a quantity of the aqueous solution comprising urea, followed by separating the urea-adsorbed-MXene from the bulk solution, for example by filtration. Or, the contacting may comprise passing the aqueous urea solution though a bed or beds or across a surface comprising one of more MXene compositions. Or the contacting may comprise a method involving both bulk and bed or surface processing.

Once the MXenes have adsorbed the urea and are separated from the aqueous solution, the MXenes may be replaced or re-generated by flushing with suitable solvents.

To this point, the description has been in terms of methods, but the invention(s) also include those devices the useful for affecting these methods. That is, certain embodiments also include those devices for removing urea from an aqueous solution of urea, the device comprising an exchangeable cartridge of MX-ene composition through or along which the solution is directed to pass, the passage being adapted to allow the urea solution to contact the MX-ene composition contained in the cartridge. These cartridges also represent embodiments of this invention, and may be configured to provide for the percolation of the aqueous solutions through bulk quantities of the MXenes, or may be configured with MXene-coated channels, along which the solutions are directed to pass. Within these devices or cartridges, the MXene composition is or comprises any one or more of the MXene compositions described herein.

Terms

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps and those that do not materially affect the basic and novel characteristic(s) of the claimed invention. Embodiments described in terms of the phrase "comprising" (or its equivalents), also provide, as embodiments, those which are independently described in terms of "consisting of" and "consisting essentially of" For those composition embodiments provided in terms of "consisting essentially of," the basic and novel characteristic(s) is the ability to remove low levels of urea from aqueous solutions in a timely manner as described herein or as explicitly specified.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

Throughout this specification, words are to be afforded their normal meaning, as would be understood by those skilled in the relevant art. However, so as to avoid misunderstanding, the meanings of certain terms will be specifically defined or clarified.

The terms "MXenes" or "two-dimensional (2D) crystalline transition metal carbides" or two-dimensional (2D) transition metal carbides" may be used interchangeably to refer collectively to compositions described herein as comprising substantially two-dimensional crystal lattices of the general formulae $M_{n+1}X_n(T_s)$, $M_2A_2X(T_s)$. and $M'_2M''_nX_{n+1}(T_s)$, where M, M', M", A, X, and $T_s$ are defined herein. Supplementing the descriptions herein, $M_{n+1}X_n(T_s)$ (including $M'_2M''_mX_{m+1}(T_s)$ compositions) may be viewed as comprising free standing and stacked assemblies of two dimensional crystalline solids. Collectively, such compositions are referred to herein as "$M_{n+1}X_n(T_s)$," "MXene," "MXene compositions," or "MXene materials." Additionally, these terms "$M_{n+1}X_n(T_s)$," "MXene," "MXene compositions," or "MXene materials" can also independently refer to those compositions derived by the chemical exfoliation of MAX phase materials, whether these compositions are present as free-standing 2-dimensional or stacked assemblies (as described further below). These compositions may be comprised of individual or a plurality of such layers. In some embodiments, the MXenes comprising stacked assemblies may be capable of, or have atoms, ions, or molecules, that are intercalated between at least some of the layers. In other embodiments, these atoms or ions are lithium.

The term "crystalline compositions comprising at least one layer having first and second surfaces, each layer comprising a substantially two-dimensional array of crystal cells" refers to the unique character of these materials. For purposes of visualization, the two-dimensional array of crystal cells may be viewed as an array of cells extending in an x-y plane, with the z-axis defining the thickness of the composition, without any restrictions as to the absolute orientation of that plane or axes. It is preferred that the at least one layer having first and second surfaces contain but a single two-dimensional array of crystal cells (that is, the z-dimension is defined by the dimension of approximately one crystal cell), such that the planar surfaces of said cell array defines the surface of the layer; it should be appreciated that real compositions may contain portions having more than single crystal cell thicknesses.

That is, as used herein, "a substantially two-dimensional array of crystal cells" refers to an array which preferably includes a lateral (in x-y dimension) array of crystals having a thickness of a single unit cell, such that the top and bottom surfaces of the array are available for chemical modification.

The following listing of Embodiments is intended to complement, rather than displace or supersede, the previous descriptions.

Embodiment 1. A method of removing urea from an initial aqueous solution of urea, the method comprising subjecting the aqueous solution of urea to a MXene composition, at ambient or near ambient temperatures and conditions, so that the urea is reduced from an initial concentration in the initial solution to a final concentration in a final solution, wherein the initial concentration of urea in the initial aqueous solution is in a range of from 10 to 20 mmol/L, from 20 to 40 mmol/L, from 40 to 80 mmol/L, from 80 to 160 mmol/L, from 160 to 200 mmol/L, from 200 to 400 mmol/L, from 400 to 600 mmol/L, from 600 to 800 mmol/L, from 800 to 1000 mmol/L, or is defined by two or more of these ranges, or is initially in a concentration range from from 5 to 10 mg/dL, from 10 to 15 mg/dL, from 15 to 20 mg/dL, from 20 to 25 mg/dL, from 25 to 30 mg/dL, from 30 to 35 mg/dL, from 35 to 40 mg/dL, from 40 to 45 mg/dL, from 45 to 50 mg/dL, from 50 to 55 mg/dL, from 55 to 60 mg/dL, from 60 to 70 mg/dL, from 70 to 80 mg/dL, from 80 to 90 mg/dL, from 90 to 100 mg/dL, or is defined by two or more of these ranges, and the final concentration is at least 10%, 20%, 30%, 40%, 50%, 60%, 70%, 80%, or 90% less than the initial concentration.

Embodiment 2. The method of Embodiment 1, wherein the MXene composition comprises a composition comprising at least one layer having first and second surfaces, each layer described by a formula $M_{n+1}X_n\ T_x$ and comprising:

a substantially two-dimensional array of crystal cells, each crystal cell having an empirical formula of $M_{n+1}X_n$, such that each X is positioned within an octahedral array of M, wherein M is at least one Group IIIB, IVB, VB, or VIB metal, wherein each X is C, N, or a combination thereof;

n=1, 2, or 3; and wherein $T_x$ represents surface termination groups.

Embodiment 3. The method of Embodiment 2, wherein the MXene composition comprises a plurality of stacked layers Embodiment 4. The method of Embodiment 2 or 3, wherein at least one of said surfaces of each layer has surface termination groups ($T_x$) comprising alkoxide, carboxylate, halide, hydroxide, hydride, oxide, sub-oxide, nitride, sub-nitride, sulfide, thiol, or a combination thereof Embodiment 5. The method of any one of Embodiments 2 to 4, wherein at least one of said surfaces of each layer has surface terminations comprising alkoxide, fluoride, hydroxide, oxide, sub-oxide, or a combination thereof Embodiment 6. The method of any one of Embodiments 2 to 5, wherein both surfaces of each layer have said surface terminations comprising alkoxide, fluoride, hydroxide, oxide, sub-oxide, or a combination thereof.

Embodiment 7. The method of any one of Embodiments 2 to 6, wherein M is at least one Group IVB, Group VB, or Group VIB metal, preferably Ti, Mo, Nb, V, or Ta.

Embodiment 8. The method of any one of Embodiments 1 to 7, wherein the MXene composition is described by a formula $M_{n+1}X_n\ T_x$, where $M_{n+1}X_n$ are $Ti_2CT_x$, $Mo_2TiC_2T_x$, $Ti_3C_2T_x$, or a combination thereof, and $T_x$ is as described herein.

Embodiment 9. The method of any one of Embodiments 2 to 7, wherein M is Ti, and n is 1 or 2, preferably 2.

Embodiment 10. The method of Embodiment 1, wherein the MXene composition comprises a composition comprising at least one layer having first and second surfaces, each layer comprising:

a substantially two-dimensional array of crystal cells, each crystal cell having an empirical formula of $M'_2M''_nX_{n+1}$, such that each X is positioned within an octahedral array of M' and M", and where $M''_n$ are present as individual two-dimensional array of atoms intercalated (sandwiched) between a pair of two-dimensional arrays of M' atoms, wherein M' and M" are different Group IIIB, IVB, VB, or VIB metals (especially where M' and M" are Ti, V, Nb, Ta, Cr, Mo, or a combination thereof), wherein each X is C, N, or a combination thereof; and n=1 or 2.

Embodiment 11. The method of Embodiment 10, wherein n is 1, M' is Mo, and M" is Nb, Ta, Ti, or V, or a combination thereof.

Embodiment 12. The method of Embodiment 10 or 11, wherein n is 2, M' is Mo, Ti, V, or a combination thereof, and M" is Cr, Nb, Ta, Ti, or V, or a combination thereof.

Embodiment 13. The method of any one of Embodiments 10 to 12, wherein $M'_2M''_nX_n+_1$ comprises $Mo_2TiC_2$, $Mo_2VC_2$, $Mo_2TaC_2$, $Mo_2NbC_2$, $Mo_2Ti_2C_3$, $Cr_2TiC_2$, $Cr_2VC_2$, $Cr_2TaC_2$, $Cr_2NbC_2$, $Ti_2NbC_2$, $Ti_2TaC_2$, $V_2TaC_2$, or $V_2TiC_2$, or a nitride or carbonitride analog thereof Embodiment 14. The method of any one of Embodiments 10 to 13, wherein $M'_2M''_nX_{n+1}$, comprises $Mo_2TiC_2$, $Mo_2VC_2$, $Mo_2TaC_2$, or $Mo_2NbC_2$, or a nitride or carbonitride analog thereof.

Embodiment 15. The method of any one of Embodiments 10 to 14, wherein $M'_2M''_nX_n+_1$ comprises $Mo_2Ti_2C_3$, $Mo_2V_2C_3$, $Mo_2Nb_2C_3$, $Mo_2Ta_2C_3$, $Cr_2Ti_2C_3$, $Cr_2V_2C_3$, $Cr_2Nb_2C_3$, $Cr_2Ta_2C_3$, $Nb_2Ta_2C_3$, $Ti_2Nb_2C_3$, $Ti_2Ta_2C_3$, $V_2Ta_2C_3$, $V_2Nb_2C_3$, or $V_2Ti_2C_3$, or a nitride or carbonitride analog thereof.

Embodiment 16. The method of any one of Embodiments 10 to 15, wherein $M'_2M''_nX_n+_1$ comprises $Mo_2Ti_2C_3$, $Mo_2V_2C_3$, $Mo_2Nb_2C_3$, $Mo_2Ta_2C_3$, $Ti_2Nb_2C_3$, $Ti_2Ta_2C_3$, or $V_2Ta_2C_3$, or a nitride or carbonitride analog thereof.

Embodiment 17. The method of any one of Embodiments 10 to 16, wherein the MXene composition comprises a plurality of stacked layers Embodiment 18. The method of any one of Embodiments 10 to 17, wherein at least one of said surfaces of each layer has surface terminations comprising alkoxide, carboxylate, halide, hydroxide, hydride, oxide, sub-oxide, nitride, sub-nitride, sulfide, thiol, or a combination thereof Embodiment 19. The method of any one of Embodiments 10 to 18, wherein at least one of said surfaces of each layer has surface terminations comprising alkoxide, fluoride, hydroxide, oxide, sub-oxide, or a combination thereof Embodiment 20. The method of any one of Embodiments 10 to 19, wherein both surfaces of each layer have said surface terminations comprising alkoxide, fluoride, hydroxide, oxide, sub-oxide, or a combination thereof.

Embodiment 21. The method of any one of Embodiments 1 to 20, wherein the MXene composition is any of the compositions described in any one of U.S. patent application Ser. No. 14/094,966 (filed Dec. 3, 2013), 62/055,155 (filed Sep. 25, 2014), 62/214,380 (filed Sep. 4, 2015), 62/149,890 (filed Apr. 20, 2015), 62/127,907 (filed Mar. 4, 2015) or International Applications PCT/US2012/043273 (filed Jun. 20, 2012), PCT/US2013/072733 (filed Dec. 3, 2013), PCT/US2015/051588 (filed Sep. 23, 2015), PCT/US2016/020216 (filed Mar. 1, 2016), or PCT/US2016/028,354 (filed Apr. 20, 2016), each of which is incorporated by reference at least for its teaching of the compositions and methods of making the same.

Embodiment 22. The method of any one of Embodiments 1 to 21, wherein the aqueous solution further comprises amino acids, polypeptides, or blood plasma proteins.

Embodiment 23. The method of any one of Embodiments 1 to 22, wherein the aqueous solution further comprises one or more of erythrocytes (red blood cells, RBCs), leukocytes (white blood cells), or thrombocytes (platelets).

Embodiment 24. The method of any one of Embodiments 1 to 23, wherein the aqueous solution further comprises one or more of such as glucose, fatty acids, and lactic acid.

Embodiment 25. The method of any one of Embodiments 1 to 24, wherein the aqueous solution is or comprises blood or a blood product (e.g., blood serum, dialysate), and the ambient or near ambient temperatures and conditions used do not compromise the utility of the blood or blood product for later use by a human patient.

Embodiment 26. The method of any one of Embodiments 1 to 25, wherein the initial concentration is a physiologically relevant concentration to a human patient.

Embodiment 27. The method of any one of Embodiments 1 to 26, wherein the final aqueous solution of urea is contacted with previously unexposed (i.e., fresh) MXene compositions.

Embodiment 28. The method of any one of Embodiments 1 to 27, final aqueous solution of urea is contacted with previously unexposed (i.e., fresh) MXene compositions more than once in a recycle scenario.

Embodiment 29. The method of any one of Embodiments 1 to 28, wherein the final concentration of the urea in the final solution is less than 100 mmol/L, less than 80 mmol/L, less than 60 mmol/L, less than 40 mmol/L, less than 20 mmol/L, less than 10 mmol/L, less than 5 mmol/L, or less than 1 mmol/L, when measured by $^1H$ NMR, the $^1H$ NMR method as being well understood by those skilled in the art, as well as those methods described as herein.

Embodiment 30. The method of any one of Embodiments 1 to 29, wherein the urea is undetectable in the final solution by $^1H$ NMR, the $^1H$ NMR method as being well understood by those skilled in the art, as well as those methods described as herein.

Embodiment 31. A device for removing urea from an aqueous solution of urea, the device comprising an exchangeable cartridge of MXene composition through which the solution is directed to pass, the passage adapted to allow the urea solution to contact the MXene composition contained in the cartridge. In certain of these Embodiments, the MXene composition is or comprises any one or more of the MXene compositions described herein.

Embodiment 32. The device of Embodiment 31, wherein the device is adapted to allow the aqueous solution of urea to percolate through at least a portion of the MXene composition.

Embodiment 33. The device of Embodiment 31 or 32, wherein the device is adapted to affect the method of any one of Embodiments 1 to 30.

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein. In particular, while the examples provided here focus on specific MXene materials, it is believed that the principles described are relevant to other such MXene materials. Accordingly, the descriptions provided here should not be construed to limit the disclosure, and the reader is advised to look to the nature of the claims as a broader description.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

Herein, we present the adsorption behavior of $Ti_3C_2T_x$ both in the aqueous solution of urea and dialysate. First-principle calculations indicated urea that has stable adsorption on MXene surface groups in both parallel and vertical orientations. The results of the adsorption studies showed rapid urea removal at low concentrations in dialysate (~30 mg/dL). The adsorption results showed that the adsorption efficiency in water was higher than in dialysate due to the competition of other biomolecules present in the dialysate. The comparison of various MXenes showed that $Ti_3C_2T_x$ had better adsorption performance in both in aqueous solutions and dialysate, compared to $Ti_2CT_x$ and $Mo_2TiC_2T_x$. Cytotoxicity assessment of MXene $Ti_3C_2T_x$ showed that, at the tested concentrations, the MXene had no significant effect on cell viability over an incubation period of 24 hours, which meant the $Ti_3C_2T_x$ has good biocompatibility and can be used in biomedical applications. Thus, $Ti_3C_2T_x$ was a promising material for removal of urea from uremic patients.

Example 1: Materials

Urea crystals were purchased from Sigma-Aldrich (99.9-101.0%, calc. on dry substance) and urea assay kit (DIUR-100) from BioAssay Systems. The dialysate samples were collected from the uremia patients (Cedars-Sinai Medical Center, Los Angeles, CA) and stored at −80° C. until used. The $Ti_3C_2T_x$ MXene and its precursors $Ti_3AlC_2$, $Mo_2TiC_2T_x$ and $Ti_2CT_x$ as well as oxidized Nanodiamond UD90 were synthesized. $Ti_3C_2T_x$ was synthesized as described previously. Briefly, 5 g of $Ti_3AlC_2$ (<37 μm particle size) powder was added into hydrofluoric acid (HF, 10%, 50 mL) solution over 2 min. The solution was stirred for 24 h at 35° C. After that, the multilayer $Ti_3C_2T_x$ was obtained by washing with deionized (DI) water by centrifugation and decantation several times until the pH of suspension reached ~6. Similarly, the $Mo_2TiC_2T_x$ and $Ti_2CT_x$ were synthesized by etching in 50% HF at 55° C. for 72 h and in 10% HF at 35° C. for 18 hr, respectively. The urea characteristic signal in the aqueous solutions before and after adsorption were determined using $^1H$-NMR (Varian Inova 500 NMR Spectrometer). The samples were prepared by adding 25 μL D20 and 475 μL urea aqueous solution to a 5 mm NMR tube. CellTiter 96© Aqueous One Solution Cell Proliferation Assay (Promega Corporation Cat. #G3580) was used to study biocompatibility. Hydrochloric acid was purified by sterilized autoclaving in media, and Ag nanoparticles were purchased from Sigma-Aldrich. ATCC murine fibroblast cell line 3T3 grown in Dulbecco's Modified Eagle Medium supplemented with foetal bovine serum, live-dead stain (Molecular Probes)-calcein-acetoxymethyl ester (calcein-AM) and ethidium homodimer-1 (EthD-1) were used to study biocompatibility.

Figure 1B:
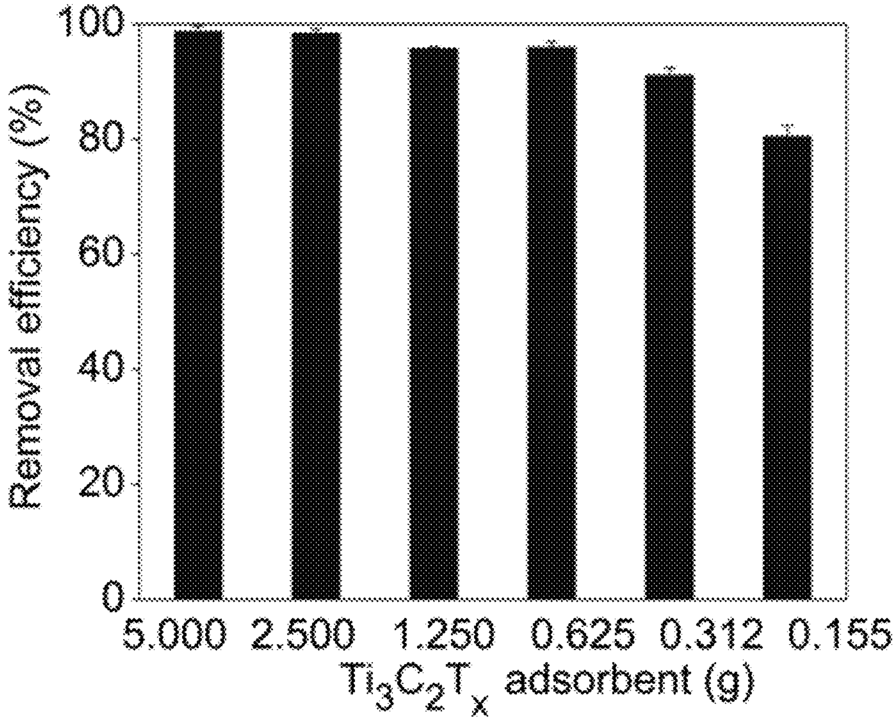
Figure 1C:
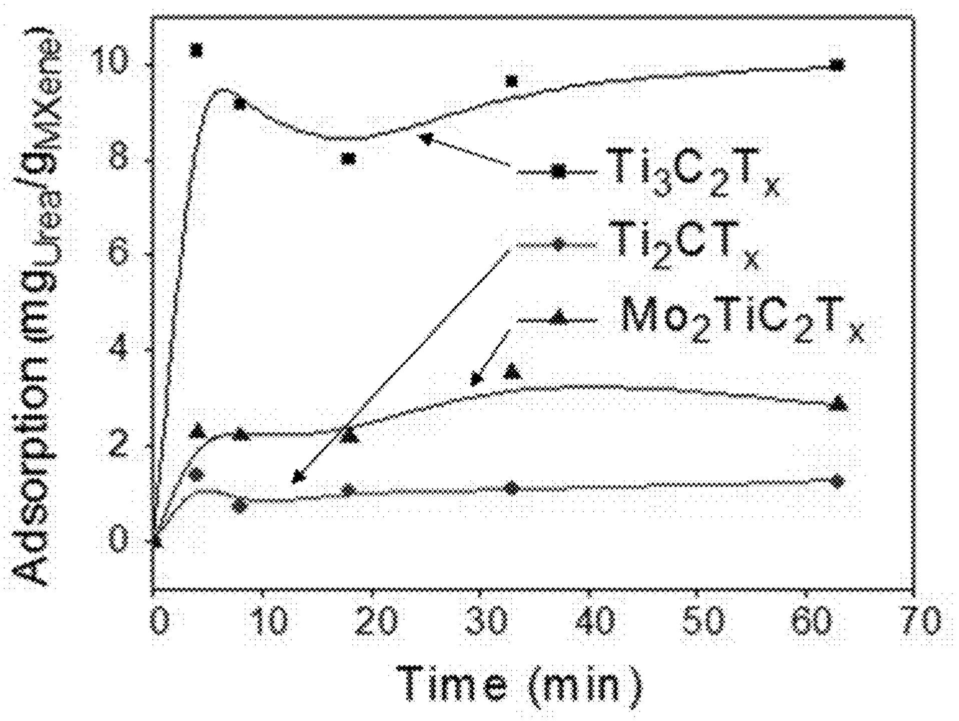
Figure 1D:
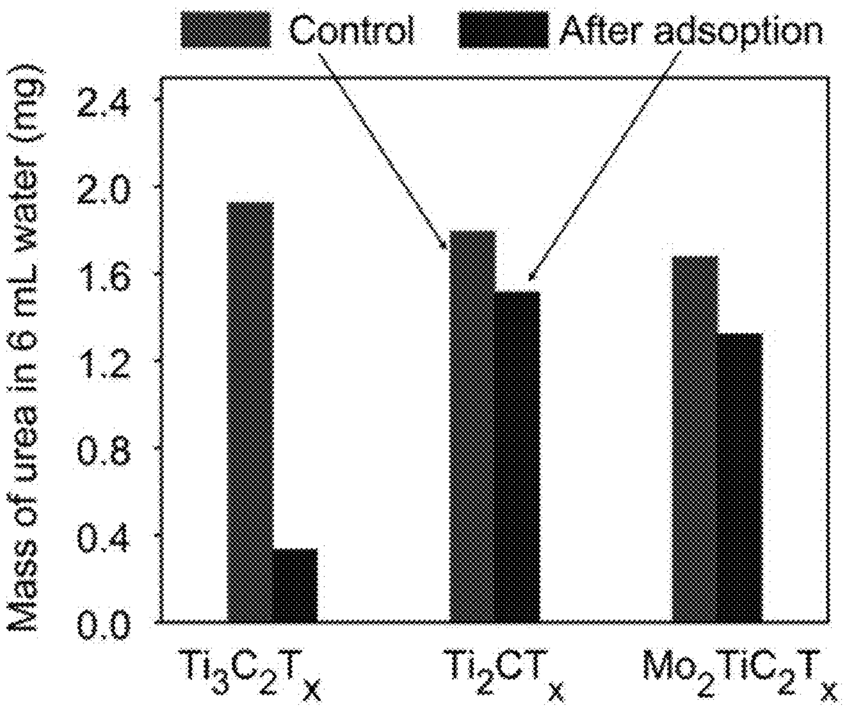

Example 1: In a first set of experiments, urea was dissolved in water to reach a 30 mg/dL urea concentration. Then different masses of MXene ($Ti_3C_2T_x$) powder (5.000, 2.500, 1.250, 0.625, 0.312 g and 0.155 g) were added into 6 mL of urea aqueous solution, mixed for 3 minutes by manual shaking and then kept on a test tube rack at room temperature. The concentration of urea was examined by reading the optical density at 520 nm using urea assay kit. At mass loadings of 5, 2.5 and 1.25 g, urea assay kit results indicated that when $Ti_3C_2T_x$ MXene with masses of 5, 2.5, 1.25 and 0.625 g were used, the urea was almost completely adsorbed (>95% adsorption) after only 4 minutes of MXene being in the solution, 3 min shaking and 1 min sitting on the test tube rack (FIG. 1A). At lower mass loading of $Ti_3C_2T_x$ powder, 0.312 and 0.155 g, urea adsorption was not as high as 95% (FIG. 1B). Similar urea adsorption was observed for all the reaction durations from 1 min to 1 h, indicating that MXene effective reaction time is less than 5 minutes. We also investigated the adsorption kinetics of two other MXenes, $Ti_2CT_x$ and $Mo_2TiC_2T_x$ and compared them with $Ti_3C_2T_x$ adsorption. The results indicate that all materials with a mass-loading of 0.155 g adsorbed urea rapidly within 4 min, after which, adsorption showed a small change by increasing the contact time indicating that an equilibrium state was obtained (FIG. 1C). The results indicate that $Ti_3C_2T_x$ shows the best adsorption performance with the highest urea removal efficiency from aqueous solution of these three MXenes (FIG. 1D)

Example 2: In a second set of experiments, dialysate from uremia patients with 30 mg/dL urea concentration was used. Similar testing steps as for the Example 2 were used: different masses of MXene ($Ti_3C_2T_x$) powder (5.000, 2.500, 1.250, 0.625, 0.312, and 0.155 g) were added into 6 mL of the dialysate solution, mixed for 3 minutes by manual shaking and then kept on a test tube rack at room temperature. The concentration of urea was examined by reading the optical density at 520 nm. Urea adsorption was measured after addition of 5.000, 2.500, 1.250, 0.625, 0.312, 0.155 g (FIG. 2A), with the mass of $Ti_3C_2T_x$ are 5.000 and 2.500 g of MXene, urea adsorption in dialysate can reach to 94%. However, when the mass of MXenes reduce under 1.250 g, the adsorption efficiency reduced dramatically to under 31% (FIG. 2B). The adsorption kinetics of two other MXenes, $Ti_2CT_x$ and $Mo_2TiC_2T_x$ were also investigated and compared with $Ti_3C_2T_x$ adsorption in dialysate. The results indicated that all materials with a mass-loading of 0.625 g adsorbed urea rapidly within 4 min, after which, adsorption showed a small change by increasing the contact time indicating that an equilibrium state was obtained (FIG. 2C). The results indicate that $Ti_3C_2T_x$ showed the best adsorption performance with the highest urea removal efficiency from dialysate solution of these three MXenes (FIG. 2D).

These initial measurements showed that $Ti_3C_2T_x$ MXene removed biologically relevant amounts of urea. It is reasonably expected that other MXenes can provide the same or maybe even more efficient adsorption. Such high adsorption ability has never been reported for any material, which makes MXene the best synthetic material to remove urea by adsorption. This process can replace the currently used dialysis procedure, allowing development of a wearable kidney for renal disease patients that currently require regular or constant dialysis treatment in a hospital.

Example 3: Computational Details

Figure 3A:
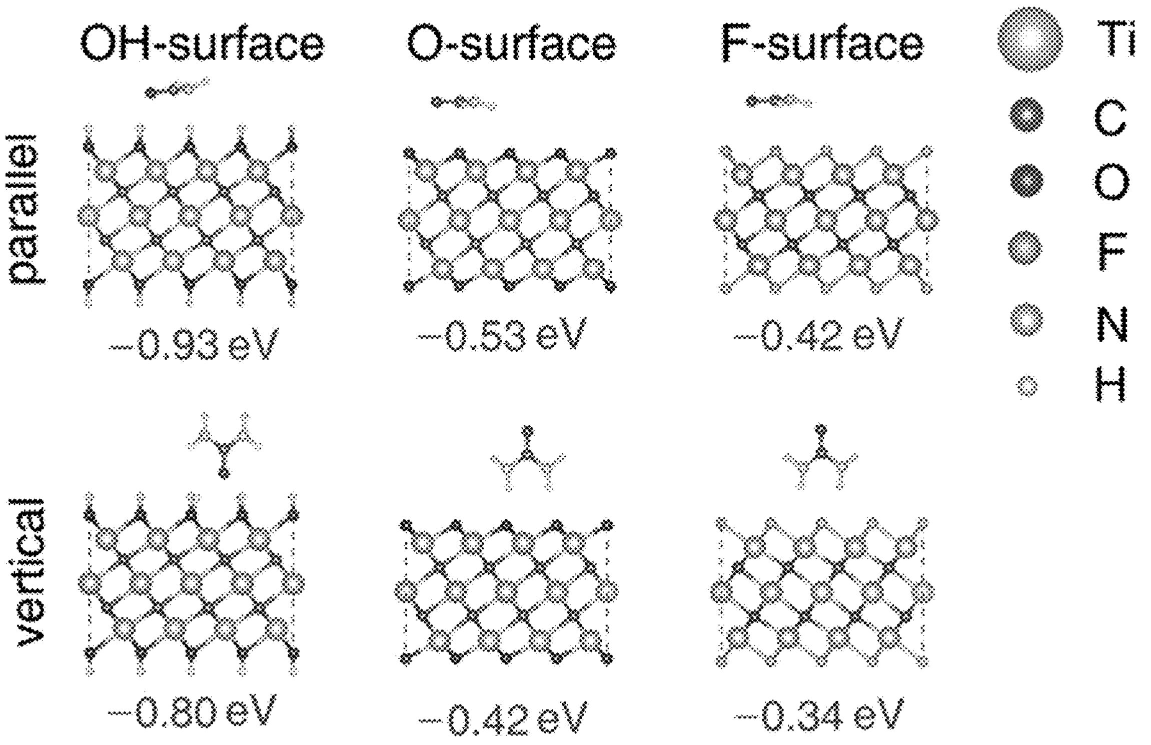
FIGS. 3A-B shows a schematic representation of computation about interaction between urea and MXenes.
Figure 3B:
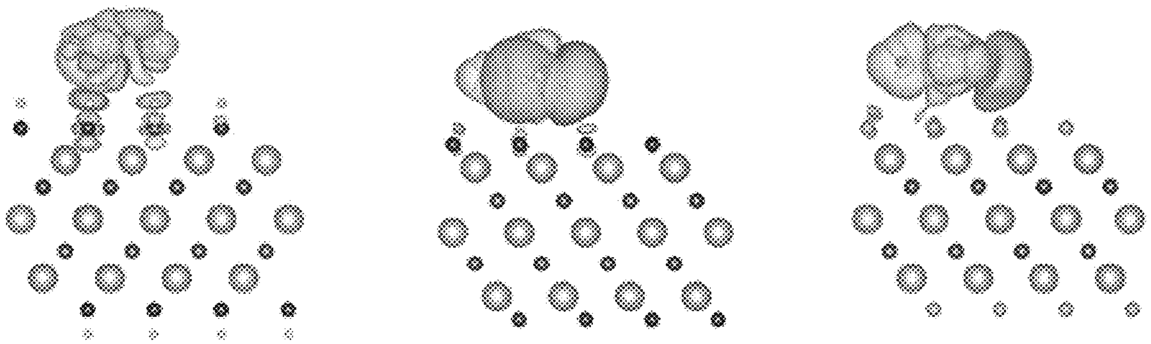
Figure 4A:
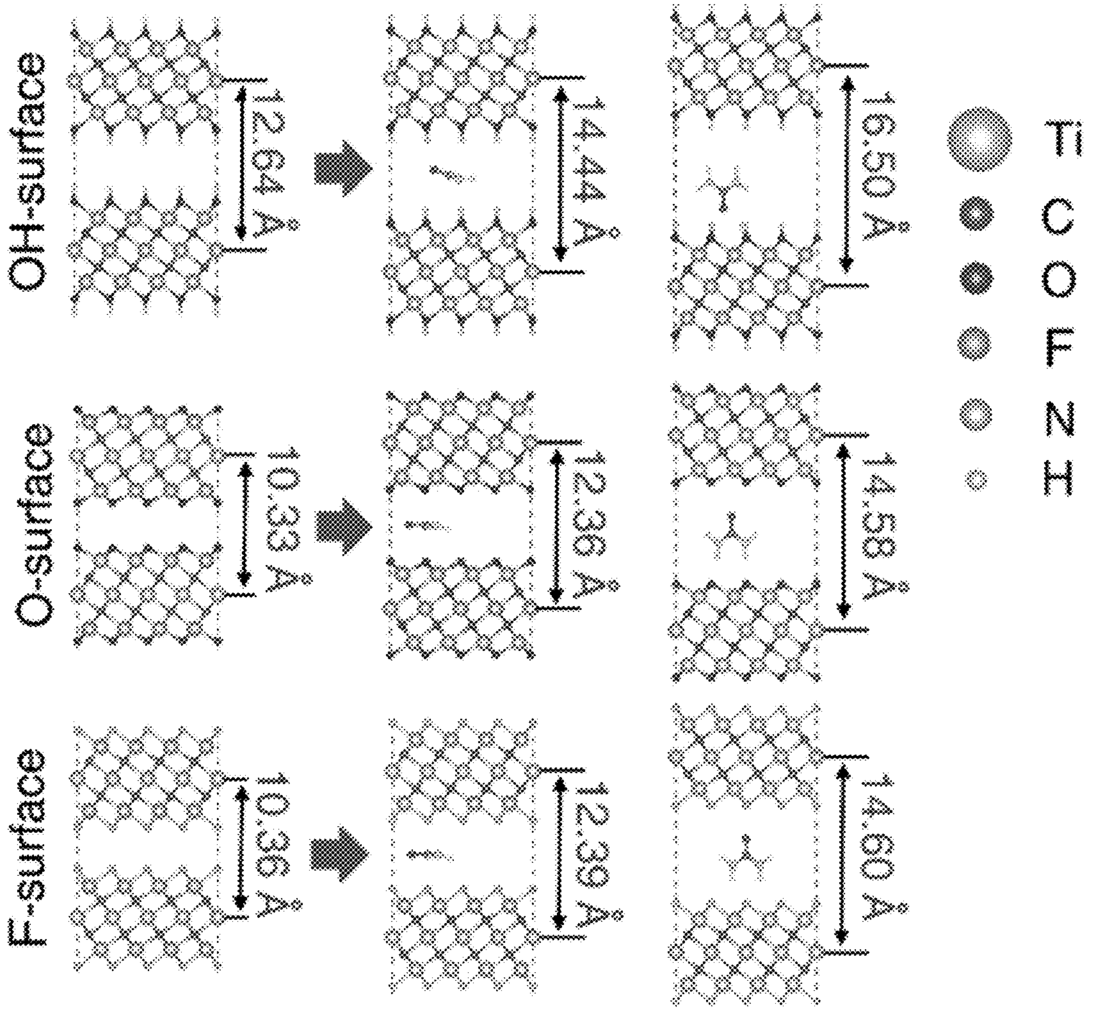
FIGS. 4A-B shows computation distances between MXenes layers.
Figure 4B:
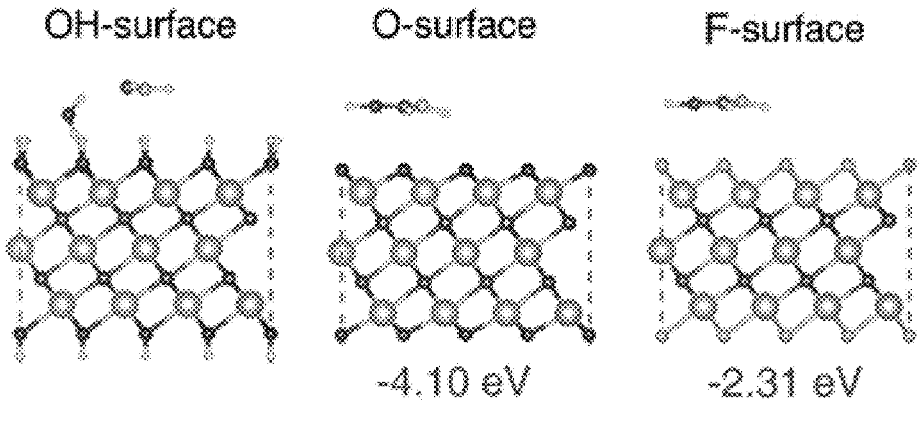
Figure 5A:
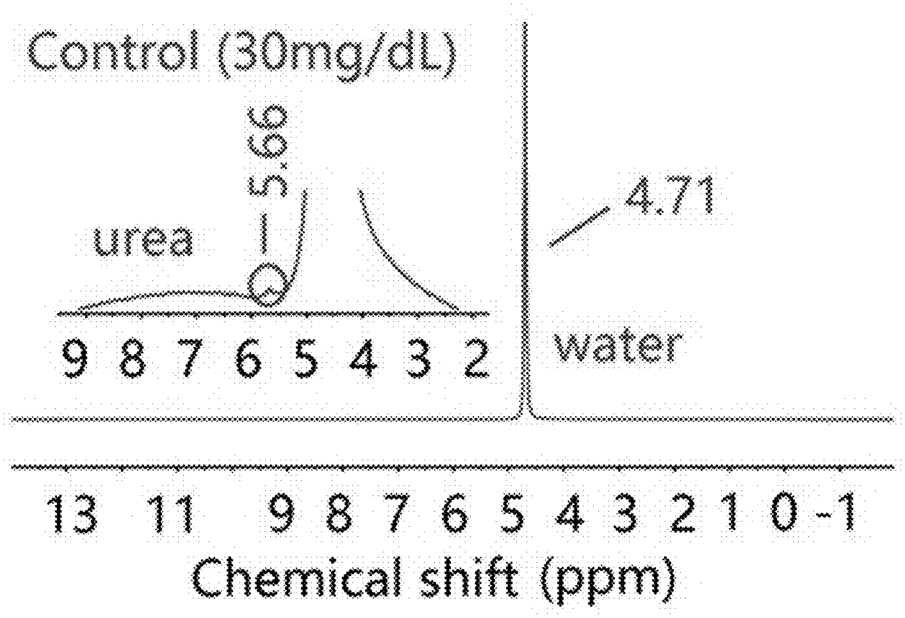
FIG. 5A shows an $^1H$ NMR spectrum of an aqueous urea solution 30 mg/dL.
Figure 5B:
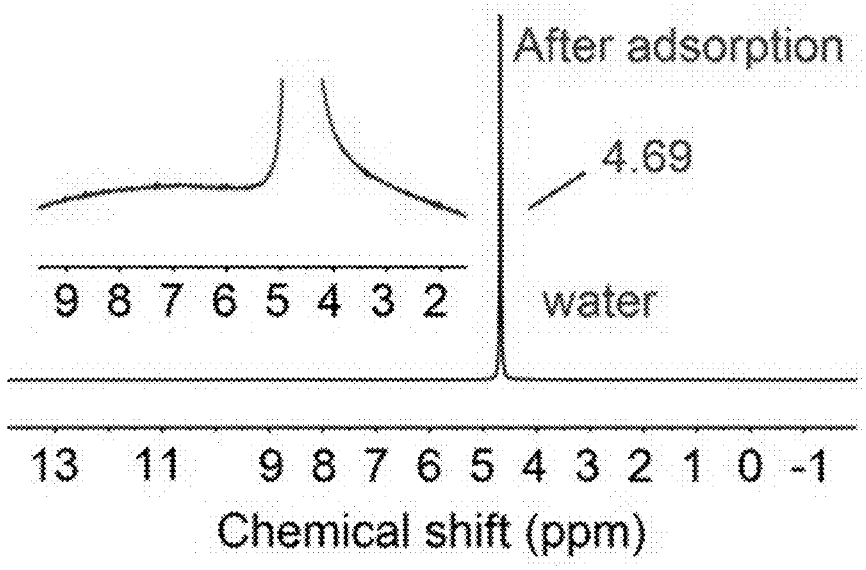
FIG. 5B shows an $^1H$ NMR spectrum after adsorption of urea from aqueous solution using $Ti_3C_2T_x$ (mass loading 0.625 g; concentration of urea 30 mg/dL; volume 6 mL).
Figure 5C:
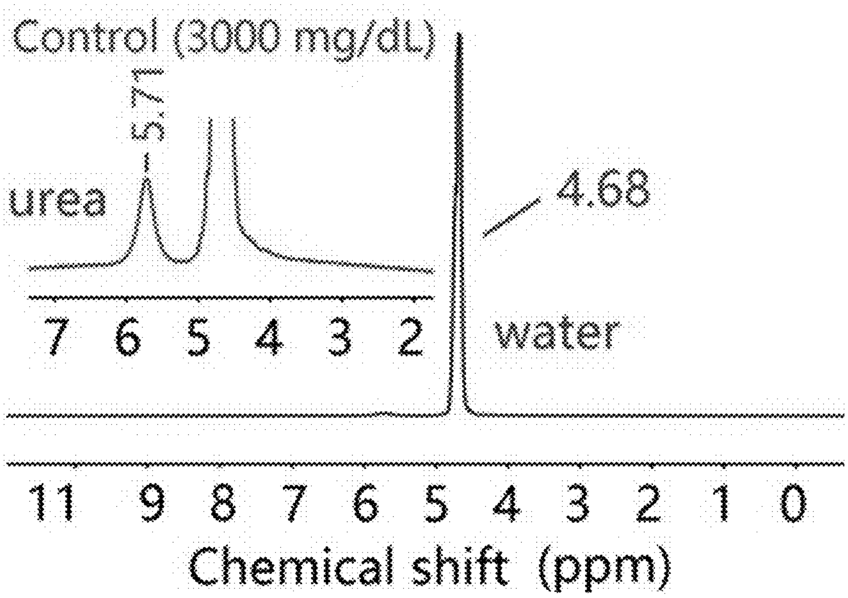
FIG. 5C shows an $^1H$ NMR spectrum of an aqueous urea solution 3000 mg/dL.
Figure 5D:
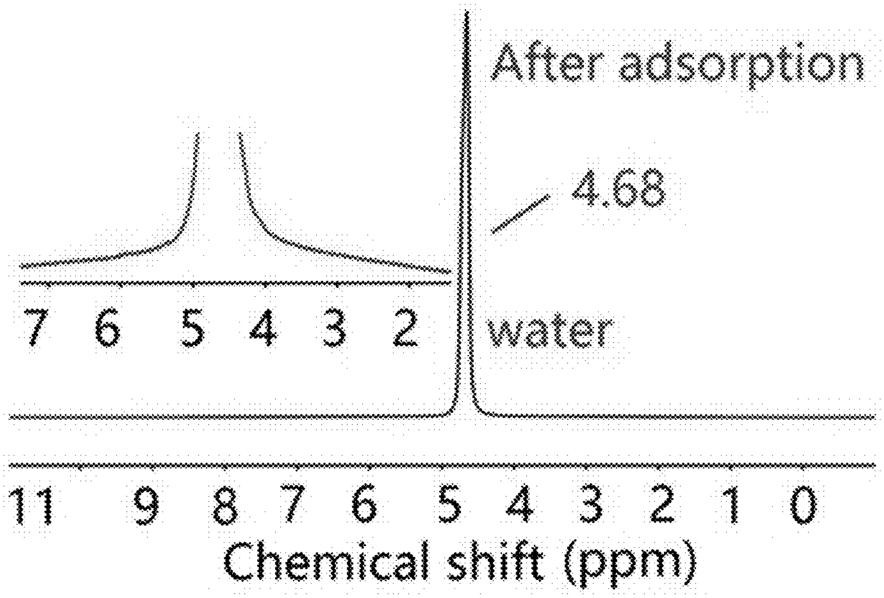
FIG. 5D shows an $^1H$ NMR spectrum after adsorption of urea from aqueous solution using $Ti_3C_2T_x$ (mass loading 0.625 g; concentration of urea 3000 mg/dL; volume 6 mL).

To understand the interaction between urea and MXenes, first-principle calculations were performed to investigate the adsorption behaviors for urea on the MXene surface. $Ti_3C_2T_x$ was chosen as the representation for the following discussions and three different surface terminations (—OH, —O or —F) are considered. The binding energy Eb of urea on MXene surface was defined as:

$$Eb=E_{MXenes+urea}-(E_{MXenes}+E_{urea}),$$

where $EM_{Xenes+urea}$ is the total energy of MXene with a urea molecular, $E_{MXenes}$ is the total energy of MXene and $E_{urea}$ is the total energy of the urea molecular. The most stable adsorption configurations for each orientation (parallel or vertical) and their binding energies are exhibited in FIG. 3A. The binding energies on different surfaces range from −0.34 to −0.93 eV. The calculations showed that regardless of surface terminations (—OH, —O or —F), the urea molecule “preferred” the parallel adsorption configurations. Moreover, urea had the most stable adsorption on OH-surface with binding energy of −0.93 and −0.8 eV for parallel and vertical orientations respectively, followed by O- and F-surfaces. This could be explained by difference of charge density as shown in FIG. 3B, showing parallel urea adsorption configuration on the surfaces of MXenes. There was a more obvious charge transfer between urea and OH-surface. Meanwhile, the urea adsorption effects on the interlayer spacing of $Ti_3C_2T_x$ were calculated. In general, presence of urea in between MXene layers expands the interlayer spacing (FIGS. 3A-3B). As urea might be protonated in acid solution, the interaction between protonated urea and $Ti_3C_2T_x$ surfaces was calculated as shown in FIGS. 4A-4B. Protonated urea will decompose on OH-surface, resulting in the formation C—$(NH_2)_2$ and $H_2O$, while has enhanced adsorption on O- or F-surface with binding energies of −4.10 and 2.31 eV respectively. In a word, MXenes were shown to have strong interactions with urea or protonated urea, consistent with MXenes acting as an effective adsorbent of urea.

Example 6: Expanded Studies—Methods

Data from the actual adsorption of urea from aqueous solutions were used to validate these theoretical calculations. To determine the efficiency of urea removal, many techniques have been adopted, such as nuclear magnetic resonance (NMR) technical, high performance liquid chromatography (HPLC) and other chemical reaction coupled colorimetric and fluorometric methods. FIGS. 5A-5D show proton nuclear magnetic resonance ($^1$H-NMR) spectrum of urea in aqueous solution at low (~30 mg/dL) and high (3,000 mg/dL) concentrations before and after urea adsorption using $Ti_3C_2T_x$. The exchange of protons between urea and water is greatly enhanced by small changes in pH. Therefore, in the presence of MXenes, which are strong Lewis acids, the urea is protonated, resulting in the proton transfer from water to urea which cause the collapse of the two peaks into a single peak. The process of urea protonation is acid-base (Schematic 1); the protonation of urea first happens on the urea acyl oxygen atom and then leads to a second protonation at one of the nitrogen atoms. As a result, the signal of urea disappeared (FIGS. 5B and 5D); however, this is not conclusive evidence of complete urea adsorption by MXenes, because it can be a signal effect caused by the pH change in the solution.

Schematic 1. Protonation process of urea in acidic solution.

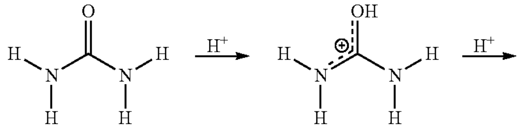

-continued

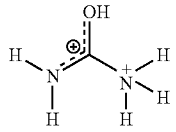

Another possible cause could stem from the terminated OH groups present on the surface of $Ti_3C_2T_x$ acting as a nucleophile, attacking the carbonyl carbon atom of the urea molecule (Schematic 2). The acid-base catalyzed reaction proceeds through a tetrahedral intermediate and formed ammonium carbamate, which causes collapse of the two peaks into a singlet. Therefore, the $^1$H-NMR measurement was not suitable for quantitative analysis. However, according to previous calculations, —OH moieties have a very strong adsorption on MXene surface with binding energy over −10 eV. Therefore, it is difficult for OH to leave MXene surface. But, it is easy to break O—H bonds.

Schematic 2. Formation of ammoniu carbamate from nucleophilic attack on urea.

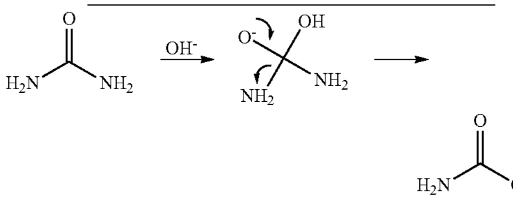

To perform the quantitative analysis of urea removal from aqueous solution, the BioAssay Systems' urea assay kit method was used. FIG. 1A shows the effect of mass-loading of $Ti_3C_2T_x$ on adsorption capacity and the comparison of urea removal efficiency from aqueous solution. The urea concentration significantly reduced with increased $Ti_3C_2T_x$ mass loading ranging 0.155-5.000 g. The adsorption efficiency by $Ti_3C_2T_x$ can reach 98% within 4 min. Even at lower mass-loading of $Ti_3C_2T_x$, 0.155 g, urea removal efficiency was as high as 80% (FIG. 1B). The adsorption capacity based on the kinetic studies is 9.7 mg/g with a lower mass-loading (0.155 g). This was indicative of almost all active sites in the MXenes being occupied. Urea adsorption capacity was likely reduced by the formation of hydrogen bonds between water molecules and the MXene, limiting the active sites available for urea absorption and also by solvation of urea.

The adsorption kinetics of two other MXenes, $Ti_2CT_x$ and $Mo_2TiC_2T_x$ were also investigated and compared with $Ti_3C_2T_x$ adsorption (FIG. 1C). The results indicated that all materials with a mass-loading of 0.155 g adsorbed urea rapidly within 4 min, after which, adsorption showed a small change by increasing the contact time indicating that an equilibrium state was obtained. The reason for the fast adsorption process is believed to be due to the presence of larger number of active groups such as —OH, —O and —F on the surface of the MXenes, which can form the hydrogen bonds with urea immediately. The results indicate that $Ti_3C_2T_x$ shows the best adsorption performance with the highest urea removal efficiency from aqueous solution of these three MXenes (FIG. 1D).

Figure 6:
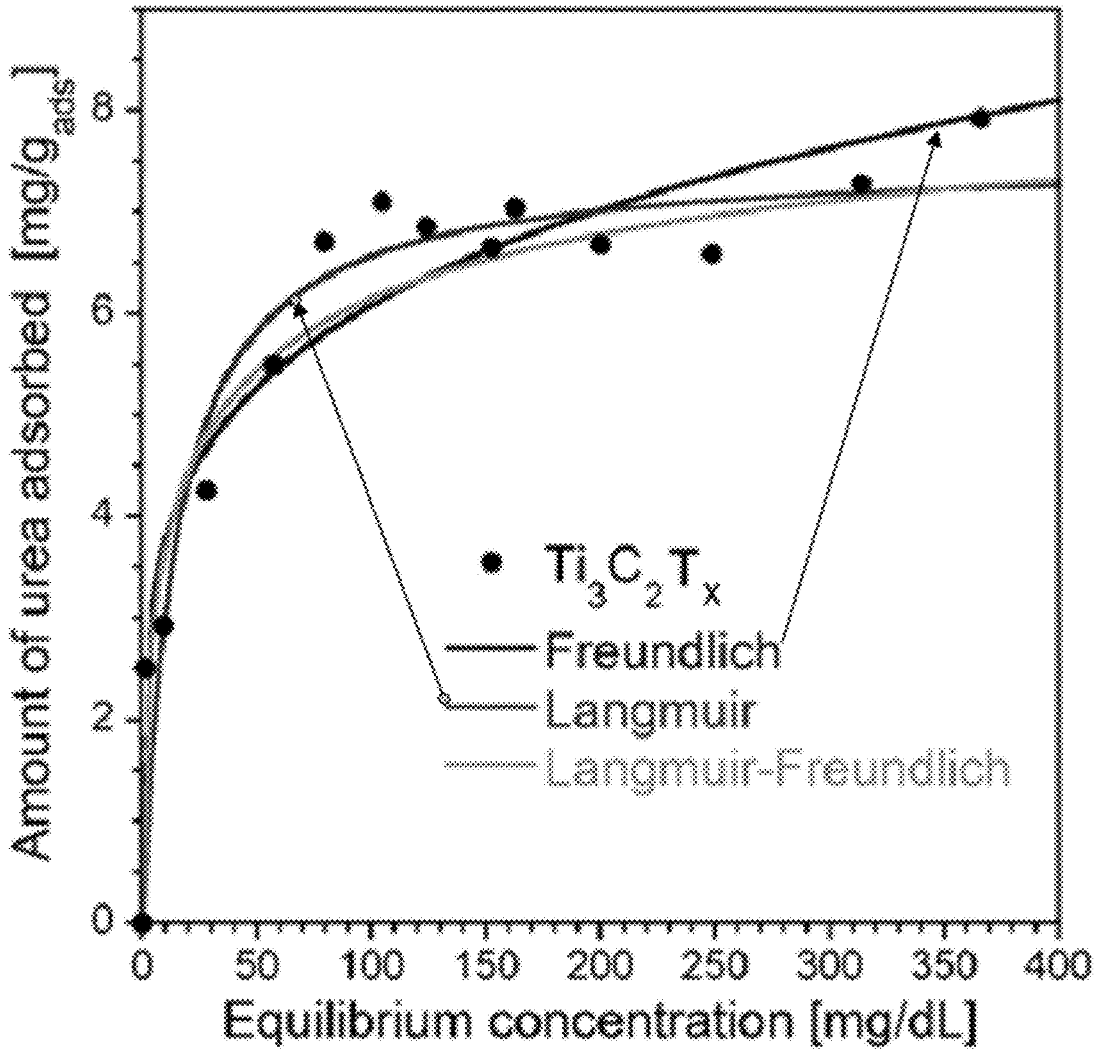
FIG. 6 shows adsorption isotherms of urea on $Ti_3C_2T_x$ (fit by Freundlich (solid blue line), Langmuir (solid red line) and Langmuir-Freundlich (solid light-blue line) models. Amount of urea adsorbed in mg per gram of adsorbent versus equilibrium concentration of urea using two-dimensional (2D) titanium carbide, $Ti_3C_2T_x$, as adsorbent (experimental points are marked with filled blue circles). The experimental adsorption data were fitted by Freundlich (solid light-blue line) for non-ideal adsorption that involves heterogeneous sorption with a non-uniform population of adsorption sites, Langmuir (solid brown line) for ideal adsorption, there are a fixed number of sites with the same adsorption energy available on the adsorbent surface and Langmuir-Freundlich (solid pink line) is a combination of the Langmuir and Freundlich isotherms.

FIG. 6 shows the equilibrium adsorption isotherm of urea on $Ti_3C_2T_x$ and fitting using Langmuir, Freundlich and Langmuir-Freundlich models. The adsorption capacity along with the corresponding constants for each model was estimated (Table 1). The Langmuir isotherm theory assumes monolayer coverage of adsorbate over a homogeneous adsorbent surface. Once a site is filled, no further sorption can take place at that site, indicating that the surface reaches a saturation point where the maximum adsorption of the surface will be achieved. The Freundlich expression isotherm theory was used to describe heterogeneous systems, which assumed that as the adsorbate concentration increases the concentration of adsorbate on the adsorbent surface will increase as well. The maximum adsorption capacities ($q_o$) of $Ti_3C_2T_x$ adsorbent calculated from the Langmuir and Langmuir-Freundlich models were found to be 7.5 mg/g and 10.4 mg/mg, respectively. By comparing the constants in Table 1 for three isotherm models, the Langmuir and Langmuir-Freundlich isotherms show similar adsorption capacity to the experimental data (9.7 mg/g), suggesting that physical sorption plays an important role in this adsorption process. The Langmuir-Freundlich isotherm model presents a better fit with a regression coefficient value ($R^2$=0.9569) higher than Langmuir ($R^2$=0.9233) and Freundlich isotherm ($R^2$=0.9449) models. The maximum adsorption capacity ($q_o$) calculated from the Langmuir-Freundlich fit closer to the experimentally determined value than the capacity calculated by other two models, suggesting the heterogeneous adsorption of urea on $Ti_3C_2T_x$ in this case. K is a constant which characterizes the strength of adsorbate binding to the adsorbent, while n is the heterogeneity factor indicating, the degree of nonlinearity between solution concentration and adsorption. A value of n<1 indicate adsorption is a physical process.

TABLE 1

Parameters of Langmuir, Freundlich and Langmuir-Freundlich models for adsorption of urea on $Ti_3C_2T_x$.

| | Langmuir (eq. 3) | | | Freundlich (eq. 4) | | | Langmuir-Freundlich (eq. 5) | | | |
|---|---|---|---|---|---|---|---|---|---|---|
| Adsorbent | $q_o$, mg/g | K, L/mg | $R^2$ | K, (mg/g) $(L/mg)^{1/n}$ | n | $R^2$ | $q_o$, mg/g | n | K, L/mg | $R^2$ |
| $Ti_3C_2T_x$ | 7.5 | 0.069 | 0.9233 | 2.35 | 0.21 | 0.9449 | 10.4 | 0.46 | 0.026 | 0.9569 |

Example 7: Expanded Studies—Adsorption of Urea from Aqueous Solution

The urea adsorption of various MXenes was tested using aqueous solutions at ambient conditions. The initial concentration of urea in aqueous solution was ~30 mg/dL, which corresponded to the normal urea concentration in the dialysate of a patient suffering from uremia. To study the kinetics and removal efficiency, different mass-loadings of MXene ($Ti_3C_2T_x$) powder (5.000, 2.500, 1.250, 0.625, 0.312 and 0.155 g—adsorbent dosage) were added into 6 mL of urea aqueous solution mixed by hand shaking (3 min) and then held static. For $Mo_2TiC_2T_x$ and $Ti_2CT_x$ materials the adsorbent dosage was 0.625 g. At 4, 9, 18, 33, and 63 min time points, the urea solutions were sampled (1 mL) using a micropipette and then centrifuged at 14,000 rpm. Afterwards, the supernatants were collected and centrifuged again (14,000 rpm) to remove small particles of adsorbent prior to analysis.

The adsorption isotherm of urea from aqueous solution was conducted only for $Ti_3C_2T_x$ which preliminary kinetic studies showed the highest removal efficiency among all MXenes studied here. The same amount of $Ti_3C_2T_x$ (0.625 g) was weighted and added to urea solutions (6 mL) ranging in concentration from 30 to 450 mg/dL. After reaching equilibrium (60 min), the samples were centrifuged, supernatants were analyzed for their urea content, and the equilibrium adsorption isotherm was constructed. Linear detection ranged from 0.08 mg/dL (13 μM) to 100 mg/dL (17 mM) urea in a 96-well plate assay. Therefore, the initial and final concentration of urea solution was tested with a dilution.

The concentration of urea (in mg/dL) was determined using BioAssay Systems' urea assay kit (DIUR-100) by reading the optical density (OD) at 520 nm following Equation 1:

$$[\text{Urea}] = \frac{OD_{sample} - OD_{blank}}{OD_{standard} - OD_{blank}} \times n \times [STD] \quad (1)$$

where $OD_{sample}$, $OD_{blank}$ and $OD_{standard}$ are OD values of sample, standard and water, respectively. The variable n is the dilution factor and [STD]=50 (or 5 for low urea samples) was the urea standard concentration (in mg/dL).

The amount adsorbed urea was calculated from Equation 2:

$$q = \frac{(C_O - C_e) \times V}{m} \quad (2)$$

where q was the amount of adsorbed urea (mg/g), $C_o$ is the initial concentration of solute (mg/dL), $C_e$ is the final concentration of solute at equilibrium (mg/dL), V is the volume aliquot adsorbate (mL) and m is the mass of adsorbent (g).

The Langmuir, Freundlich, and Langmuir-Freundlich adsorption isotherm equations were employed to fit experimental adsorption data. The equations of Langmuir, Freundlich and Langmuir-Freundlich isotherms are shown in Equations 3, 4, and 5 respectively $$\frac{q_e}{q_o} = \frac{KC_e}{(1 + KC_e)} \quad (3)$$

$$q = KC^n \quad (4)$$

$$\frac{q_e}{q_o} = \frac{(KC_e)^n}{1 + (KC_e)^n} \quad (5)$$

where $q_e$ is the adsorbed amount of urea per gram of adsorbent at equilibrium, $q_o$ is the maximum adsorption of urea per gram of the adsorbent, K is the Langmuir-type constant defined by the Van't Hoff equation, and the exponential term n represents the heterogeneity of the site energies.

Example 8: Adsorption of Urea from Dialysate

The urea removal adsorption efficiency was tested in dialysate of uremic patients directly. The method of testing was the same as described above for aqueous solutions. The concentration of urea (in mg/dL) was determined using BioAssay Systems' urea assay kit.

Figure 2A:
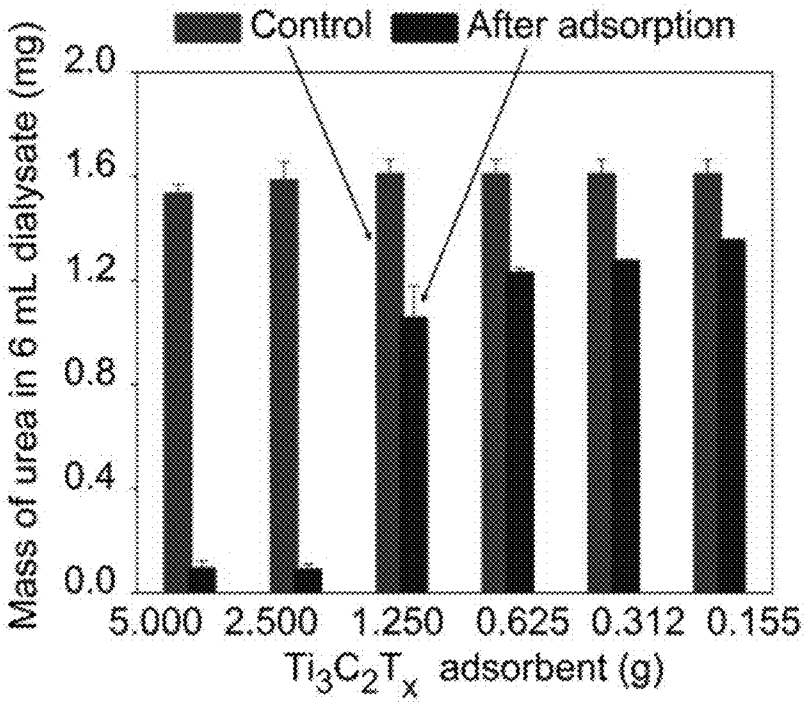
FIGS. 2A-D show the adsorption of urea from dialysate (in 6 mL; initial concentration ~30 mg/dL).
Figure 2B:
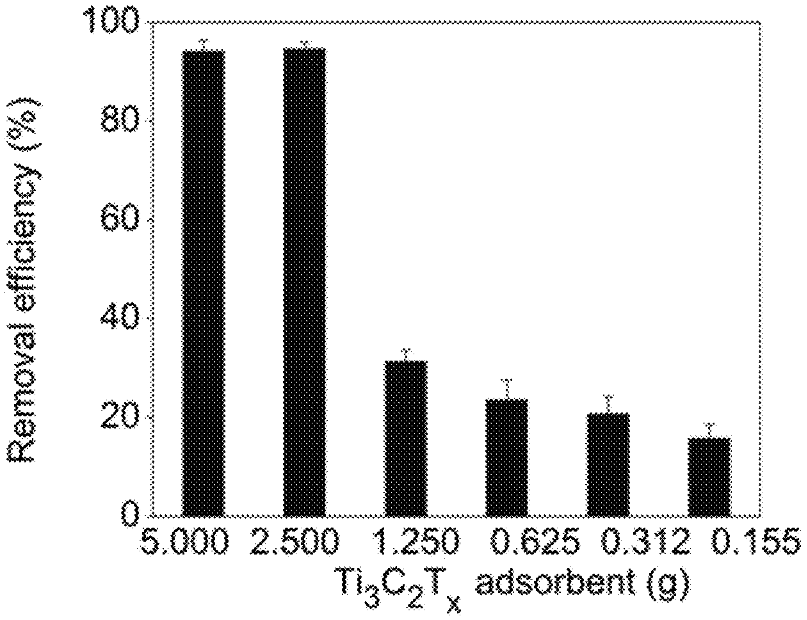
Figure 2C:
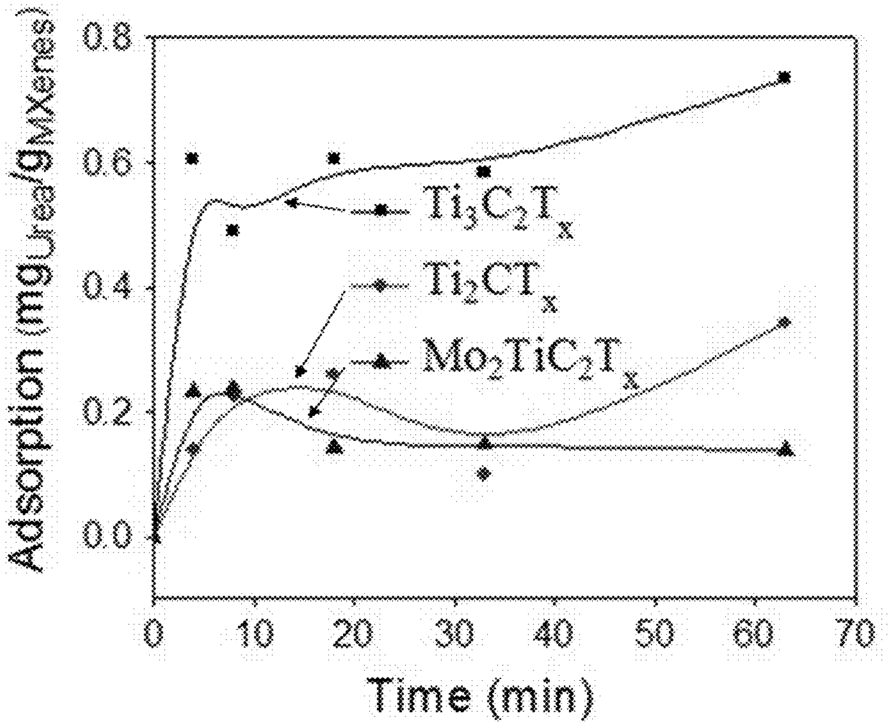
Figure 2D:
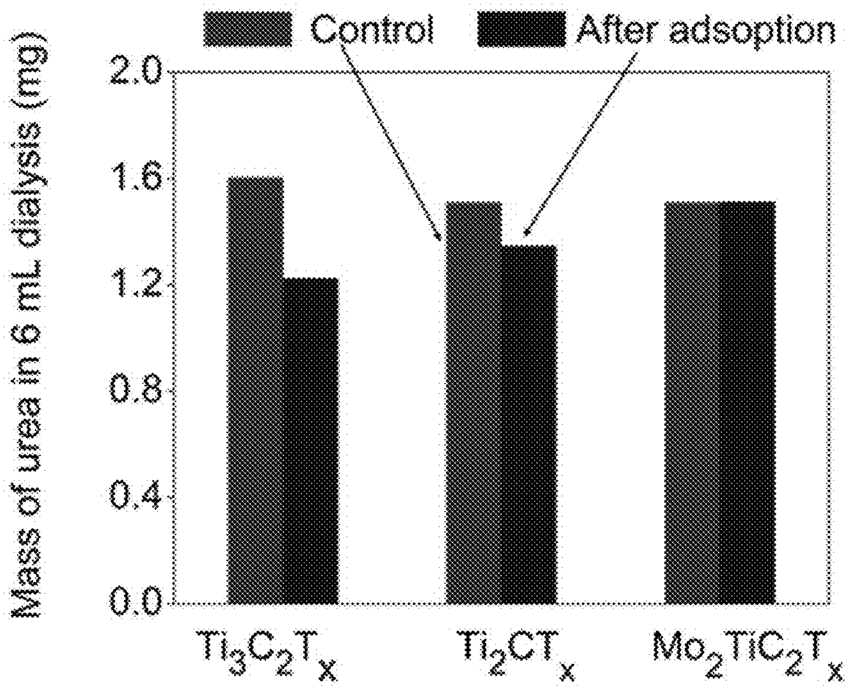

FIG. 2A shows the effect of mass-loading of $Ti_3C_2T_x$ on the removal efficiency of urea in dialysate. The urea concentration in dialysate reduces significantly for the mass loading of both 2.500 g and 5.000 g. For these two mass loadings, the removal efficiency of urea for $Ti_3C_2T_x$ is 94%, while at lower mass loading, it reduced to 15% (FIG. 8B). For 5.000 and 2.500 g $Ti_3C_2T_x$ mass loadings, urea adsorption efficiency did not change significantly from dialysate (94%) to aqueous solution (98%). However, at lower mass loadings, the removal efficiency of urea from dialysate decreased significantly compared to the adsorption of urea from aqueous solution. Moreover, the adsorption capacity of urea from dialysate reduced to 1.6 mg/g, a significant decrease compared to the adsorption of urea from aqueous solution (9.7 mg/g) for the same mass-loading (0.155 g). It is worth mentioning that the adsorption capacity of urea from dialysate increased rapidly in the first 4 min, after which it slightly increases (FIG. 2C). The lower adsorption capacity in dialysate compared to aqueous solution (compare FIG. 1C and FIG. 2C) could be related to replacement of adsorbed competing molecules in the dialysate, i.e., the ions in the dialysate compete with urea to occupy the adsorption sites. Similar adsorption kinetic behavior was observed for all three MXenes (FIG. 2C) with a fast and efficient removal within 4 min. Of those tested, the best MXene adsorbent for urea from dialysate was $Ti_3C_2T_x$, which outperformed $Ti_2CT_x$ and $Mo_2TiC_2T_x$ (FIG. 2D). In general, adsorption capacities of these MXenes were comparatively low. However, in adsorption processes the kinetics of adsorption was as important as adsorption capacity, therefore, the performance of a WAK could be improved by decreasing the time of the adsorption.

Example 9: Cytotoxicity Assessment of MXene $Ti_3C_2T_x$

A stock suspension (1 mg/mL) of each nanomaterial (GNP, GO, GO-Ag, MXene and AgNP) in media was sonicated for 30 minutes and diluted 1:2.5 in media to a concentration of 400 μg/mL. 3T3 cells were seeded in a 96-well plate at a density of $1 \times 10^4$ cells/well and incubated for 24 hours at 37° C. Spent medium was removed and 100 μL of fresh medium was added to each well. 100 μL of each nanomaterial suspension was added to triplicate wells at varying concentrations (6.25, 12.5, 25, 50, 100 and 200 μg/mL) and plates were incubated for 24 hours at 37° C., 5% $CO_2$. The NP suspension was removed, and wells were washed with sterile phosphate buffered saline. MTS reagent was diluted 1 in 6 in media, and 120 μL was added to each well. The plates were wrapped in foil and incubated for 2 hours at 37° C., 5% $CO_2$. The reagent was then transferred to a fresh 96 well plate to avoid interference of any NPs adhered to the cell surface on the base of the wells since the NPs tended to increase the absorbance readings. Absorbance was read on a BioRad plate reader at a wavelength of 490 nm. The live-dead stain was prepared in PBS to a concentration of 1 μM, and 100 μL of solution was added to each of the wells of the 96 plates prepared as for the MTS assay. Fluorescent imaging was carried out using confocal microscopy. Statistical analysis was conducted on Graphpad Prism software and a two-way ANOVA of % cell viability.

Figure 7:
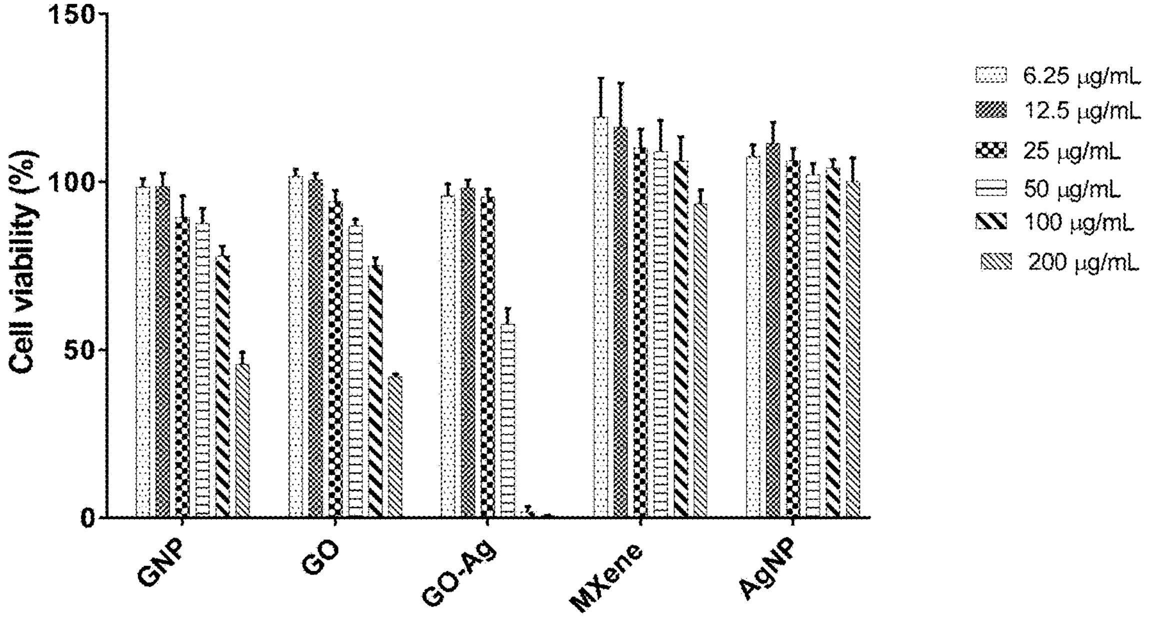
FIG. 7 shows cell viability measurement on direct contact of murine 3T3 fibroblast with $Ti_3C_2T_x$ indicating no significant reduction in cell viability following exposure to increasing concentrations of $Ti_3C_2T_x$ in contrast to graphene nanoparticles (GNP), graphene oxide (GO), and GO-Ag where a significant reduction occurred at the higher concentrations ($p<0.001$) ($n=3$, mean+/−sem).
Figure 8A:
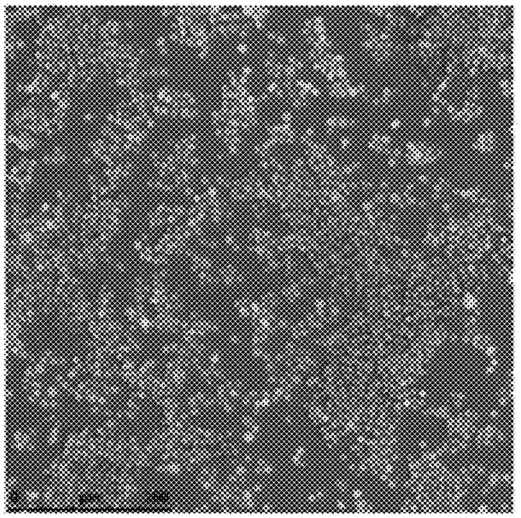
FIGS. 8A-B shows overlay confocal images combining light, red and green fluorescent micrographs to show nanoparticles (NPs) and live/dead cell staining with calcein-AM (1 μM) and ethidium homodimer (0.5 μM) in the no NPs control cells (FIG. 8A) and in MXene exposed cells at a NP concentration of 6.25 mg $mL^{-1}$ (FIG. 8B). The black NPs are clearly visible in the light microscopy overlay whilst the green fluorescence indicates a metabolizing cell fraction under the NP layer in both b and c. No red fluorescence indicating cell death was observed in the NP images.
Figure 8B:
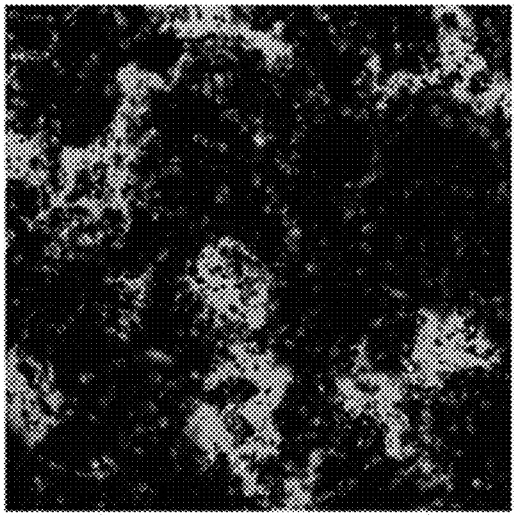

In the concentration range tested, MXene had no impact on 3T3 cell metabolism as indicated in FIG. 7 and FIG. 8A-B. In contrast GO-Ag induced a significant reduction in cell viability at concentrations of 50 μg/mL and above. GO and GNP also produced a significant reduction in cell viability at concentrations of 200 μg/ml. AgNP did not have a significant impact on cell metabolism in the concentration range used.

In this way, MXenes have been shown to be the first synthetic material that can completely remove urea from blood/dialysate at the clinical levels. Due to its very strong sorption capability, very small amounts of MXene are needed to remove urea by adsorptive process.

As those skilled in the art will appreciate, numerous modifications and variations of the present invention are possible in light of these teachings, and all such are contemplated hereby. All references cited within this specification are incorporated by reference in their entireties for all purposes, or at least for their teachings in the context of their recitation.

What is claimed:

1. A cartridge for removing urea from an initial aqueous solution of urea, comprising:

A MXene composition through which the initial aqueous solution is directed to pass, the cartridge adapted to allow the initial aqueous urea solution to contact the MXene composition contained in the cartridge;

Wherein the MXene composition is comprised in a permeable bed.

2. The cartridge of claim 1, wherein the cartridge is exchangeable.

3. The cartridge of claim 1, wherein the MXene composition comprises a composition comprising at least one layer having first and second surfaces, each layer described by a formula $M_{n+1}X_nT_x$, such that each X is position within an octahedral array of M, wherein M is at least on Group IIIB, IVB, VB, or VIB metal, wherein each X is C, N, or a combination thereof, n=1, 2, or 3; and wherein $T_x$ represents surface termination groups.

4. The cartridge of claim 3, wherein a surface termination group comprises alkoxide, carboxylate, halide, hydroxide, hydride, oxide, sub-oxide, nitride, sub-nitride, sulfide, thiol, or a combination thereof.

5. The cartridge of claim 3, wherein M is at least one group IVB, Group VB, or Group VIB metal.

6. The cartridge of claim 3, wherein Mis Ti, Mo, Nb, V or Ta, or a combination thereof.

7. The cartridge of claim 3, wherein $M_{n+1}X_n$ is $Ti_2C$, $Mo_2Ti_2C$, $Mo_2TiC_2$, $Ti_3C_2$, or a combination thereof.

8. The cartridge of claim 1, wherein the MXene composition comprises a composition comprising at least one layer having first and second surfaces, each layer comprising:

a. a substantially two-dimensional array of crystal cells, b. each crystal cell having an empirical formula of $M'_2M''_nX_{n+1}$, such that each X is positioned within an octahedral array of M' and M'', and where $M''_2$ are present as individual two-dimensional array of atoms intercalated between a pair of two-dimensional arrays of M' atoms, c. wherein M' and M'' are different Group IIIB, IVB, VB, or VIB metals, d. wherein each X is C, N, or a combination thereof; and e. n=1 or 2.

9. The cartridge of claim 8, wherein n is 1, M' is Mo, and M'' is Nb, Ta, Ti, or V, or a combination thereof.

10. The cartridge of claim 8, wherein n is 2, M' is Mo, Ti, V, or a combination thereof, and M'' is Cr, Nb, Ta, Ti, or V, or a combination thereof.

11. The cartridge of claim 8, wherein $M'_2M''_nX_{n+1}$ comprises $Mo_2TiC_2$, $Mo_2VC_2$, $Mo_2TaC_2$, $Mo_2NbC_2$, $Mo_2Ti_2C_3$, $Cr_2TiC_2$, $Cr_2VC_2$, $Cr_2TaC_2$, $Cr_2NbC_2$, $Ti_2NbC_2$, $Ti_2TaC_2$, $V_2TaC_2$, $Mo_2Ti_2C_3$, $Mo_2V_2C_3$, $Mo_2Nb_2C_3$, $Mo_2Ta_2C_3$, $Cr_2Ti_2C_3$, $Cr_2V_2C_3$, $Cr_2Nb_2C_3$, $Cr_2Ta_2C_3$, $Nb_2Ta_2C_3$, $TizNb_2C_3$, $Ti_2Ta_2C_3$, $V_2Ta_2C_3$, $V_2Nb_2C_3$, or $V_2Ti_2C_3$, or a nitride or carbonitride analog thereof.

12. The cartridge of claim 8, wherein the MXene composition comprises a plurality of stacked layers.

13. The cartridge of claim 8, wherein at least one of said surfaces of each layer has surface terminations comprising alkoxide, carboxylate, halide, hydroxide, hydride, oxide, sub-oxide, nitride, sub-nitride, sulfide, thiol, or a combination thereof.

14. A method, comprising contacting an initial aqueous urea solution to a cartridge according to claim 1, the contacting being at ambient or near ambient temperatures and under such conditions that the urea is reduced from an initial concentration in the initial aqueous urea solution to a final concentration in a final solution, wherein the initial concentration of urea in the initial aqueous solution is in a range of from 10 mmol/L to 1000 mmol/L, or is initially in a concentration range from 15 to 40 mg/dL mg/dL, and the final concentration is at least 10% less than the initial concentration, and wherein the aqueous solution is or comprises blood or a blood product and the ambient or near ambient temperatures and conditions used do not compromise the utility of the blood or blood product for later use by a human patient.

15. The method of claim 14, wherein the final concentration is at least 50% less than the initial concentration.

16. The method of claim 14, wherein the contacting is for less than about 5 minutes.

17. The method of claim 14, wherein adsorption of the urea to the MXene attains equilibrium within 5 minutes.

* * * * *